(12) United States Patent
Guan et al.

(10) Patent No.: US 9,921,191 B2
(45) Date of Patent: Mar. 20, 2018

(54) GAS CHROMATOGRAPHIC (GC) UNIT, SCALABLE GC SYSTEMS USING SAME, AND RELATED METHODS

(71) Applicant: Agilent Technologies, Inc., Santa Clara, CA (US)

(72) Inventors: Xiao-Sheng Guan, Shanghai (CN); Qiang Xu, Shanghai (CN)

(73) Assignee: Agilent Technologies, Inc., Santa Clara, CA (US)

( * ) Notice: Subject to any disclaimer, the term of this patent is extended or adjusted under 35 U.S.C. 154(b) by 243 days.

(21) Appl. No.: 14/721,833

(22) Filed: May 26, 2015

(65) Prior Publication Data

US 2015/0338382 A1    Nov. 26, 2015

(30) Foreign Application Priority Data

May 26, 2014 (CN) .......................... 2014 1 0225584

(51) Int. Cl.
*G01N 30/28* (2006.01)
*G01N 30/02* (2006.01)
(Continued)

(52) U.S. Cl.
CPC ........... *G01N 30/28* (2013.01); *G01N 30/606* (2013.01); *G01N 30/6095* (2013.01);
(Continued)

(58) Field of Classification Search
CPC .. G01N 30/28; G01N 30/606; G01N 30/6095; G01N 2030/8881; G01N 2030/025
See application file for complete search history.

(56) References Cited

U.S. PATENT DOCUMENTS 5,431,712 A    6/1995  Henderson et al.
6,497,138 B1 * 12/2002  Abdel-Rahman .... G01N 30/466
                                                              73/23.26
(Continued)

FOREIGN PATENT DOCUMENTS

CN    101641596 A    2/2010
CN    202811312 U    3/2013
(Continued)

OTHER PUBLICATIONS

John V. Hinshaw, "Comprehensive Two-Dimensional Gas Chromatography", GC Connections, www.lcgceurope.com (Feb. 2004) pp. 2-7.

(Continued)

*Primary Examiner* — Peter MacChiarolo
*Assistant Examiner* — Nathaniel Kolb

(57) ABSTRACT

A gas chromatographic (GC) unit or module may include one or more microfluidic devices, a GC column, and a flow controller (FC) comprising an FC input port for controlling fluid flows and pressures. The GC unit may be reconfigurable to provide different functionalities. The GC unit may be fluidly coupled to various other fluidic devices, such as other GC units, sample inlets, GC detectors, and the like. Multiple GC units and other fluidic devices may be utilized to build GC devices and associated systems of flexible, reconfigurable, and scalable architecture, thereby enabling a variety of modes of operation useful for present and future GC method development.

13 Claims, 18 Drawing Sheets

(51) Int. Cl.
*G01N 30/32* (2006.01)
*G01N 30/60* (2006.01)
*G01N 30/88* (2006.01)

(52) U.S. Cl.
CPC ......... *G01N 30/32* (2013.01); *G01N 30/6039* (2013.01); *G01N 2030/025* (2013.01); *G01N 2030/324* (2013.01); *G01N 2030/8881* (2013.01)

(56) References Cited

U.S. PATENT DOCUMENTS

| | | | |
|---|---|---|---|
| 7,132,650 B1 * | 11/2006 | Gamble | G01N 30/7233 137/625.46 |
| 8,343,258 B2 | 1/2013 | Guan | |
| 2002/0164816 A1 | 11/2002 | Quake | |
| 2003/0188587 A1 | 10/2003 | Manz | |
| 2005/0223821 A1 | 10/2005 | Manz | |
| 2007/0163663 A1 | 7/2007 | Strand et al. | |
| 2016/0153439 A1 | 6/2016 | Witt et al. | |

FOREIGN PATENT DOCUMENTS

| | | |
|---|---|---|
| CN | 202822862 U | 3/2013 |
| EP | 1178309 A1 | 2/2002 |
| WO | 2005016532 A2 | 2/2005 |
| WO | 2008067296 A2 | 6/2008 |
| WO | 2009154984 A1 | 12/2009 |

OTHER PUBLICATIONS

Chinese-language Office Action issued in counterpart Chinese Application No. 201410225584.2 dated Dec. 4, 2017, with Search Report (six (6) pages).

* cited by examiner

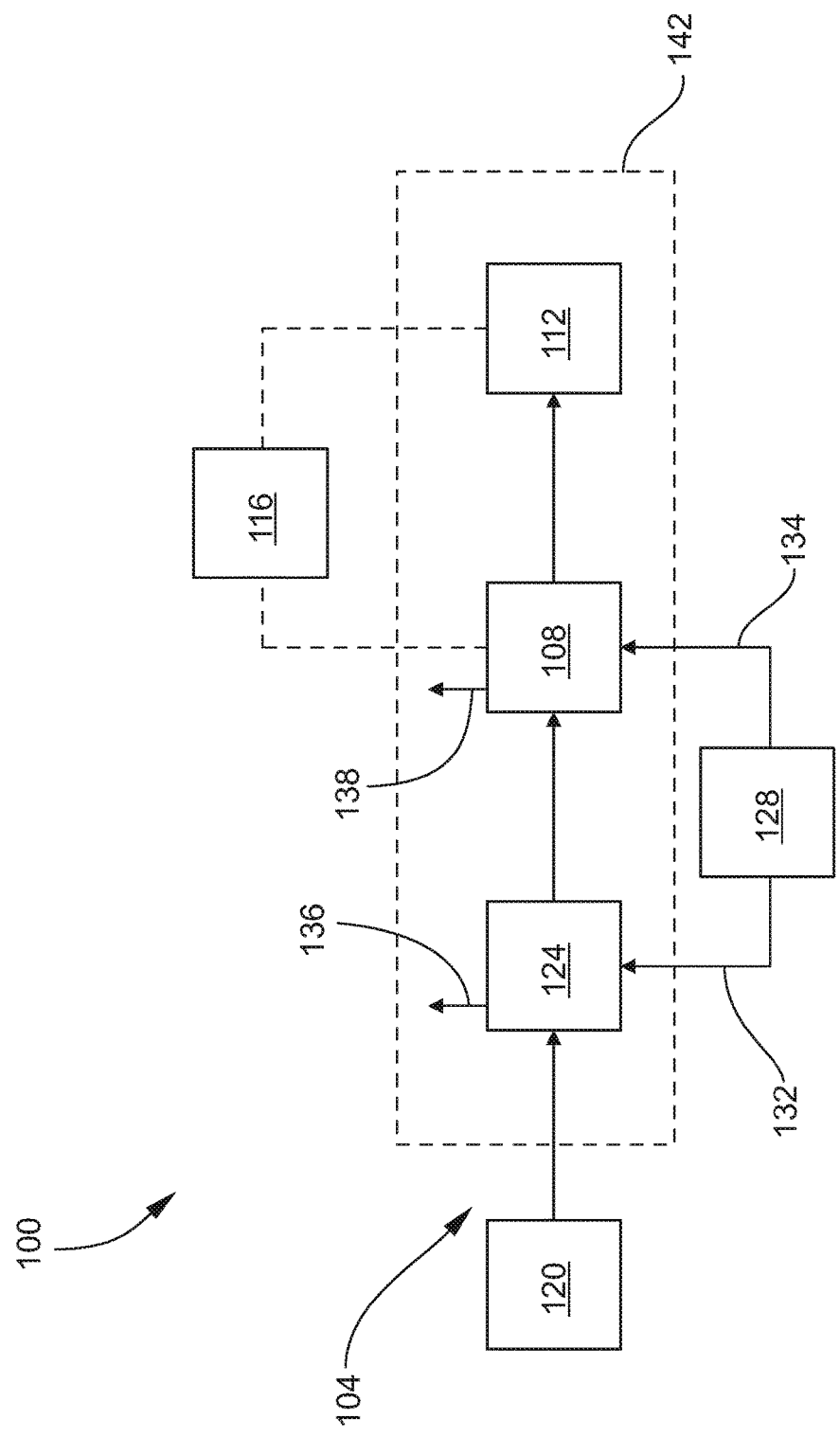

GAS CHROMATOGRAPHIC (GC) UNIT, SCALABLE GC SYSTEMS USING SAME, AND RELATED METHODS

RELATED APPLICATIONS

This application claims the benefit under 35 U.S.C. 119 of Chinese Patent Application No. 201410225584.2, filed May 26, 2014, titled "GAS CHROMATOGRAPHIC (GC) UNIT, SCALABLE GC SYSTEMS USING SAME, AND RELATED METHODS," the content of which is incorporated by reference herein in its entirety.

TECHNICAL FIELD

The present invention relates generally to gas chromatography (GC), and more particularly to the application of gas-phase microfluidics to GC.

BACKGROUND

Gas chromatography (GC) entails the analytical separation of a vaporized or gas-phase sample that is injected into a chromatographic column. The column is typically a metal, glass, or quartz tube containing a stationary phase (a coating or packing) formulated for chromatographic activity. The column is typically housed in a thermally controlled oven or may be heated directly by a heating element such as a resistive wire. A chemically inert carrier gas, such as helium, nitrogen, argon, or hydrogen, is utilized as the mobile phase for elution of the analyte sample in the column. Typically, the sample and carrier gas are separately introduced into a GC inlet coupled to the column head. In the GC inlet, the sample is injected into the carrier gas stream and the resulting sample-carrier gas mixture flows through the column. The typical GC inlet is configured for vaporizing an initially liquid-phase sample, and may provide a liner configured for performing pre-column separation as well. During column flow the sample encounters the stationary phase in the column, which causes different components of the sample to separate according to different affinities with the stationary phase. The separated components elute from the column exit and are measured by a detector, producing data from which a chromatogram or spectrum identifying the components may be constructed.

A single GC column may be inadequate for separating a target compound from a sample. In this case, a multidimensional (MDGC) GC system including two or more GC columns and respective downstream detectors may be utilized, such as a comprehensive two-dimensional (GC×GC) system. The different GC columns may have different characteristics such as length, inside diameter, and/or type of stationary phase material. For example, in a GC×GC system one column may include a polar stationary phase while the other column includes a nonpolar stationary phase. During an appropriate interval of time, a portion of the effluent from the first column containing a target compound may be diverted into the second column and ultimately to the corresponding second detector by implementing a heart-cutting technique as appreciated by persons skilled in the art.

Multidimensional GC systems may utilize fluidic switches for implementing heart-cutting, as well as for other operational modes such as flow spitting, backflushing, etc. Fluidic switches may operate in conjunction with, or may be integrated with, microfluidic devices designed to conduct sample and/or carrier gas flows to and from GC columns, detectors, and other components of a multidimensional GC system. Multidimensional GC systems may also utilize flow control devices, often electronic pneumatic controllers (EPCs), to regulate mass flow rates, forward pressures, and back pressures in relation to the columns and other fluidic devices.

It is generally difficult for users of GC systems to correctly configure a multi-column system involving the use of microfluidic devices and flow control devices such as EPCs. It is also difficult for users to apply microfluidics to compact or even oven-less GCs, as all current microfluidic devices must rely on a relatively large, forced convection GC oven (air bath) to facilitate column coupling and to prevent microfluidic devices from becoming cold spots in the sample path. Moreover, current GC instruments lack a fundamentally scalable design that would be useful for supporting the growing sophistication of analytical tasks enabled by microfluidics, such as multidimensional GC and multiple independent column heating zones.

In view of the foregoing, there is a need for GC components and methods that enable or facilitate the design and building of GC devices and systems that provide various functionalities to meet current and future requirements.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a gas chromatographic (GC) unit includes: an inlet-side microfluidic device comprising a plurality of inlet-side channels and a plurality of inlet-side ports, each inlet-side port communicating with at least one of the inlet-side channels; an outlet-side microfluidic device comprising a plurality of outlet-side channels and a plurality of outlet-side ports, each outlet-side port communicating with at least one of the outlet-side channels; a column comprising a column inlet coupled to a first inlet-side port of the plurality of inlet-side ports, and a column outlet coupled to a first outlet-side port of the plurality of outlet-side ports; and a flow controller (FC) comprising an FC input port for receiving a flow of carrier gas, a first FC output port communicating with the FC input port, and a second FC output port communicating with the FC input port, wherein the first FC output port communicates with an additional inlet-side port of the plurality of inlet-side ports.

According to another embodiment, a gas chromatographic (GC) device includes: a GC unit according to any of the embodiments disclosed herein; and a fluidic device selected from the group consisting of: a fluidic or microfluidic device communicating with at least one of the inlet-side ports or outlet-side ports; a sample introduction device communicating with at least one of the inlet-side ports; a detector communicating with at least one of the outlet-side ports; an additional GC unit communicating with at least one of the inlet-side ports or outlet-side ports; a transfer line threadedly engaged with at least one of the inlet-side microfluidic device and the outlet-side microfluidic device; and two or more of the foregoing.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic view of an example of a gas chromatograph (GC) system according to some embodiments.

DETAILED DESCRIPTION

Figure 2A:
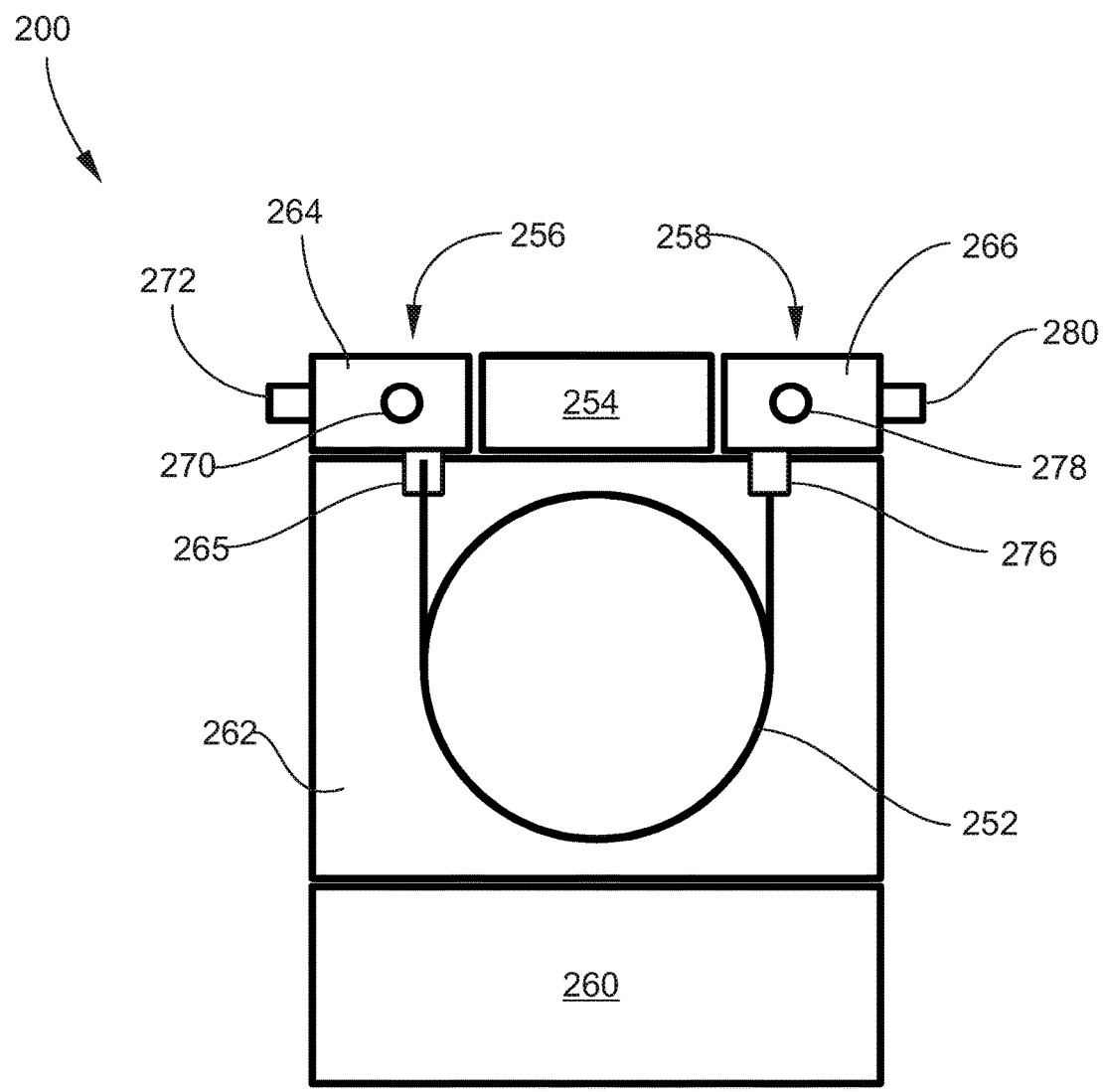
FIG. 2A is a schematic front elevation view of an example of a GC unit according to some embodiments.

In the context of the present disclosure, the term "analyte" refers generally to any sample molecule of interest to a researcher or user of a gas chromatograph (GC)—that is, a molecule on which an analysis is desired such as, for example, a chromatographic or chromatographic/mass spectral analysis. The term "sample" or "sample matrix" refers to any substance known or suspected of containing analytes. The sample may include a combination of analytes and non-analytes. The term "non-analytes" or "non-analytical components" in this context refers to components of the sample for which analysis is not of interest because such components do not have analytical value and/or may impair (e.g., interfere with) the analysis of the desired analytes. Non-analytes may generally be any molecules not of interest such as contaminants or impurities. Examples of non-analytes may include, but are not limited to, contaminants, impurities, water, oils, solvents, carrier gases, or other media, as well as stationary phase material that has bled from a chromatographic column.

In the present disclosure, the term "fluid" is used in a general sense to refer to any material that is flowable through a conduit. A "gas" is an example of a "fluid." As used herein, the term "gas" encompasses vapors, and gases in which vapors, droplets or particles may be entrained. In the present disclosure, the term "fluid" is used interchangeably with the term "gas" unless indicated otherwise.

As used herein, the term "channel" refers to any type of conduit that defines a path for fluid to flow from one point to another point. In some embodiments, a channel may be a "microfluidic channel" or "microchannel." The cross-section (or flow area) of a microchannel may have a characteristic dimension on the order of micrometers (e.g., up to about 1000 μm, or 1 mm) or lower (e.g., nanometers). For example, the characteristic dimension may range from 100 nanometers to 1000 μm (1 mm). Flow rates through the microchannel may be on the order of milliliters per minute, microliters per minute, nanoliters per minute, or lower (picoliters per minute or femtoliters per minute). The term "channel" encompasses, but is not limited to, microchannels. The term "characteristic dimension" refers to a type of dimension that is appropriately descriptive for the shape of the cross-section of a channel—for example, diameter in the case of a circular cross-section, major axis in the case of an elliptical cross-section, or a maximum width or height between two opposing sides in the case of a polygonal cross-section. The cross-section of the channel may have any of these shapes. Additionally, the cross-section of the channel may have an irregular shape, either deliberately or as a result of the limitations of fabrication techniques. The characteristic dimension of an irregularly shaped cross-section may be taken to be the dimension characteristic of a regularly shaped cross-section that the irregularly shaped cross-section most closely approximates (e.g., diameter of a circle, major axis of an ellipse, width or height of a polygon, etc.).

In typical embodiments, a microchannel is formed in a solid body of material. The material may be of the type utilized in various fields of microfabrication such as microfluidics, microelectronics, micro-electromechanical systems (MEMS), and the like. The composition of the material may be one that is utilized in these fields as a semiconductor, electrical insulator or dielectric, vacuum seal, structural layer, or sacrificial layer. The material may thus be composed of, for example, a metalloid (e.g., silicon or germanium), a metalloid alloy (e.g., silicon-germanium), a carbide such as silicon carbide, an inorganic oxide or ceramic (e.g., silicon oxide, titanium oxide, or aluminum oxide), an inorganic nitride or oxynitride (e.g., silicon nitride or silicon oxynitride), various glasses, or various polymers. In some embodiments, the material is optically transparent for a purpose such as performing an optics-based measurement, performing a sample analysis, detecting or identifying a substance flowing through the microchannel, enabling a user to observe flows, etc. The solid body of material may initially be provided in the form of, for example, a substrate, a layer disposed on an underlying substrate, a microfluidic chip, a die singulated from a larger wafer of the material, etc.

The microchannel may be formed in a solid body of material by any technique, now known or later developed in a field of microfabrication, which is suitable for the material's composition and the size and aspect ratio of the microchannel. As non-limiting examples, the microchannel may be formed by an etching technique such as focused ion beam (FIB) etching, deep reactive ion etching (DRIE), or a micromachining technique such as mechanical drilling, laser drilling or ultrasonic milling. Depending on the length and characteristic dimension of the microchannel to be formed, the etching or micromachining may be done in a manner analogous to forming a vertical or three-dimensional "via" partially into or entirely through the thickness of the material (e.g., a "through-wafer" or "through-substrate" via). Alternatively, an initially open channel or trench may be formed on the surface of a substrate, which is then bonded to another substrate to complete the microchannel. The other substrate may present a flat surface, or may also include an initially open channel that is aligned with the open channel of the first substrate as part of the bonding process. The microchannel may be defined (or bounded) directly by one or more walls of a solid body of material. Alternatively, the microchannel may be defined by the inside surface of a tube or capillary, i.e., the tube or capillary wall is the solid body of material in which the microchannel is formed. In the latter case, the tube or capillary may reside in a closed bore or open bore (e.g., a trench, groove or recess) that is formed by one or more walls of another solid body of material.

Depending on its composition, the material defining the microchannel may be inherently chemically inert relative to the fluid flowing through the microchannel. Alternatively, the microchannel may be deactivated as part of the fabrication process, such as by applying a suitable coating or surface treatment/functionalization so as to render the microchannel chemically inert. Coatings and surface treatments/functionalizations for such purposes are readily appreciated by persons skilled in the art.

In the present disclosure, the term "fluidic device" generally encompasses any device that provides or receives a flow of fluid or otherwise provides one or more fluid flow paths. Examples of fluidic devices include devices that supply a fluid flow (e.g., sample introduction device), devices that receive a fluid flow (e.g., GC detector), devices that control and/or alter a fluid flow (e.g., valves, microfluidic devices), etc. The term "microfluidic device" generally encompasses any device in which one or more microchannels are formed. A microfluidic device may include a solid body as described above and one or more ports configured for fluidic coupling with conduits or other fluidic devices.

FIG. 1 is a schematic view of an example of a gas chromatograph (GC) system 100 according to some embodiments. The GC system 100 may generally include a sample introduction system 104, a GC device 108, one or more detectors 112, and a computing device 116. The sample introduction system 104 may include a sample introduction device 120 and a GC inlet 124. The GC device 108 includes one or more GC units, embodiments of which are described below by way of examples. Generally, each GC unit includes a GC column, one or more microfluidic devices providing flow paths to and from the GC column and components external to the GC unit (e.g., sample introduction system 104, detector 112, etc.), and a flow control device or module (or flow controller, or FC) such as an electronic pneumatic controller (EPC) providing a flow rate and pressure control through the GC column and microfluidic devices. A carrier gas source 128, which may represent a carrier gas reservoir and associated components (e.g., tubing, valves, pumps, flow controllers, etc.), supplies one or more flows of carrier gas to the GC inlet 124 and the GC device 108 at regulated flow rates and/or pressures via respective carrier gas supply lines 132 and 134. The GC inlet 124 and the GC device 108 may each include one or more vents 136 and 138 for purging gases.

Certain components of the GC system 100, such as the GC unit(s) (GC column(s), microfluidic devices, flow controller(s)) of the GC device 108 and the detector(s) 112 (depending on the type of detector), may be enclosed in a housing or enclosure 142. The housing 142 may be a GC oven, which typically includes a heating device configured for maintaining the GC column at a desired temperature setting or for varying the temperature of the GC column according to a desired (predetermined, programmable) temperature profile, such as for balancing parameters such as elution time and measurement resolution. Conventionally, the heating device is configured for heating the interior of the GC oven and thereby controlling the temperature of the GC column and other components indirectly (e.g., by forced convection). In other embodiments, the heating device is configured for heating the GC column directly. For example, the heating device may include a resistive heating element mounted in thermal contact with the GC column. In addition, the microfluidic devices of the GC device 108 may include heating devices. For example, a heating device may be positioned in the structure of the microfluidic device or mounted to a side of the microfluidic device, or the microfluidic device may be positioned inside a heating device. In embodiments utilizing direct heating devices, the housing 142 may be a GC oven that additionally includes a conventional indirect heating device, which may be operated in conjunction with or as an alternative to the direct heating devices. In some embodiments, certain components of the GC system 100 such as the GC unit(s) may be mounted to a wall of the housing 142. In such embodiments, the housing 142 may be a pre-existing or commercially available GC oven retrofitted with the GC device 108 or modified or adapted as needed to operate with the GC device 108.

The sample introduction device 120 may be any device configured for injecting a sample into the GC inlet 124. Sample injection may be carried out on an automated, semi-automated or manual basis. The sample introduction device 120 may, for example, include a manually operated syringe or a syringe that is part of an automated sampling apparatus (or "autosampler"). A sample source may be located upstream of the sample introduction device 120, or may be one or more sample containers (e.g., vials) provided at the sample introduction device 120. In the latter case, the sample containers may be loaded on a carousel or other device that selects a desired sample for injection into the GC inlet 124.

The GC inlet 124 may have any configuration suitable for introducing the sample flow from the sample introduction device 120 into the carrier gas flow from the carrier gas source 128. The GC inlet 124 may process the sample/carrier gas mixture in a variety of ways as appreciated by persons skilled in the art. The GC inlet 124 may have a split, splitless, or split/splitless (S/SL) configuration. The GC inlet 124 may be located or partially located in the housing (or oven) 142, in which case the GC inlet 124 may be enclosed in a thermally insulating cup. The carrier gas may be any gas suitable for serving as an inert mobile phase that facilitates transport of the sample through the GC column(s) as appreciated by persons skilled in the art. Examples of carrier gases include, but are not limited to, helium, nitrogen, argon, and hydrogen.

The detector 112 may any detector suitable for detecting peaks eluting from the GC column 108. Examples of detectors include, but are not limited to, flame ionization detectors (FID), thermal conductivity detectors (TCD), nitrogen phosphorous detectors (NPD), electron capture detectors (ECD), flame thermionic detectors (FTD), flame photometric detectors (FPD), atomic emission detectors (AED), etc. Generally, a wide variety of detectors may be utilized, and the illustrated detector 112 may represent a combination of two or more different types of detectors. In some embodiments, the detector 112 is, or is part of, an analytical instrument such as, for example, a mass spectrometer (MS), an ion mobility spectrometer (IMS), etc. Thus, in some embodiments, the GC system 100 may be a hyphenated system such as a GC-MS, GC-IMS, or GC-IM-MS system.

The computing device 116 may have any configuration suitable for controlling various components of the GC system 100, such as components of the sample introduction system 104, GC device 108, detector(s) 112, carrier gas source 128, etc. Hence, the computing device 116 may be in signal communication with various components via wired or wireless communication. One or more modules or components of the computing device 116 may be, or be embodied in, for example, a desktop computer, laptop computer, portable computer, tablet computer, handheld computer, mobile computing device, personal digital assistant (PDA), smartphone, etc. The computing device 116 may be configured for receiving measurement signals from the detector(s) 112. The computing device 116 may also be schematically representative of a data acquisition system, display/readout device, and other components associated with generating chromatograms and spectra as appreciated by persons skilled in the art. The computing device 116 may also be configured for providing and controlling a user interface that provides screen displays with which a user may interact.

Figure 2B:
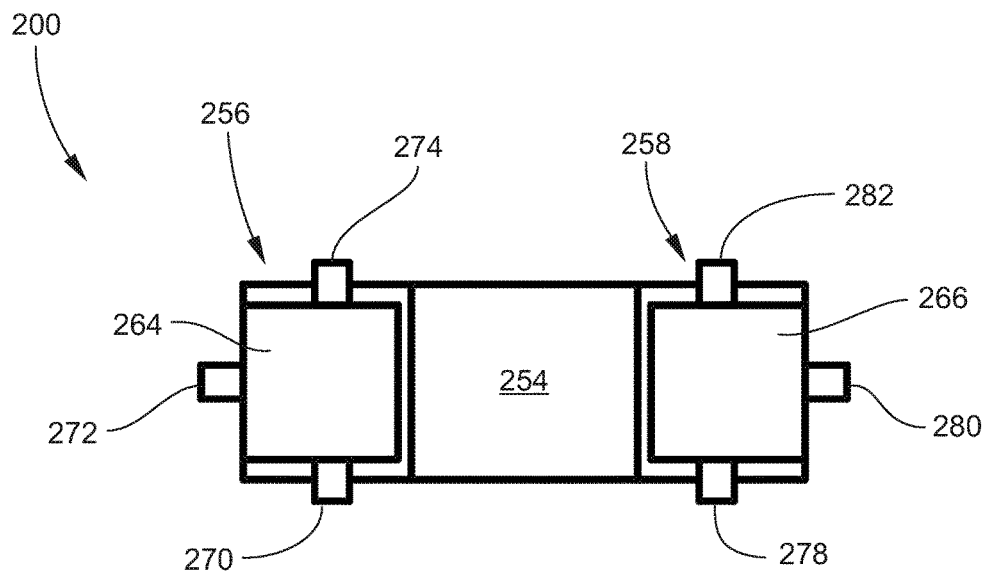
FIG. 2B is a schematic top plan view of the GC unit illustrated in FIG. 2A.
Figure 2C:
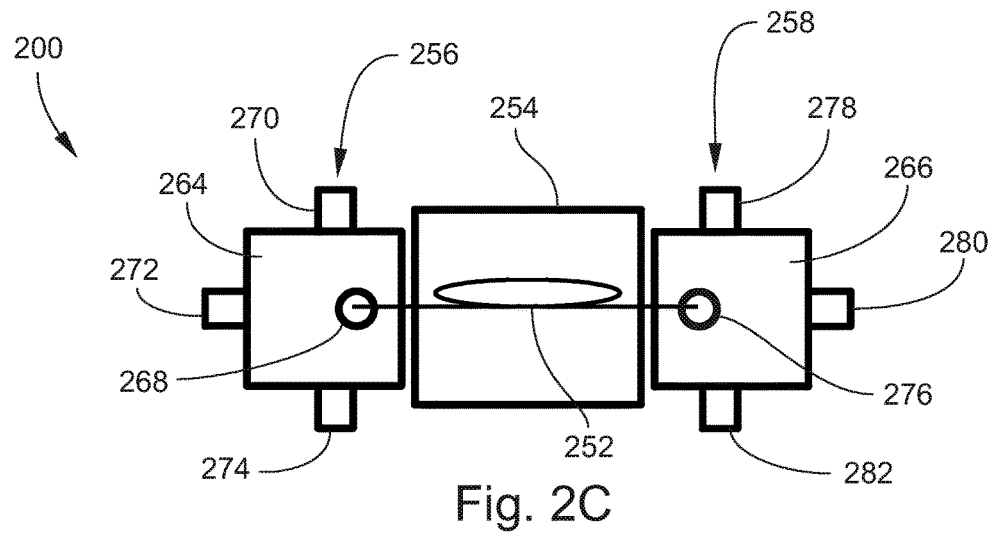
FIG. 2C is a schematic bottom plan view of the GC unit illustrated in FIG. 2A.

FIGS. 2A to 2C are a schematic front elevation view, top plan view, and bottom plan view, respectively, of an example of a GC unit 200 according to some embodiments. The GC unit 200 may generally include a GC column 252, a flow controller (FC) 254 (or flow control device, flow control module), and one or more microfluidic devices. In the present embodiment, the GC unit 200 includes an inlet-side (or first) microfluidic device 256 and an outlet-side (or second) microfluidic device 258. The GC unit 200 may also include local electronics 260 (i.e., electronics integrated with or mounted to the GC unit 200) communicating with the FC 254 (and, if provided, a heating element and/or temperature sensor associated with the GC column 252), or at least includes electrical components configured for providing a signal communication interface between the GC unit 200 and a system controller (e.g., the computing device 112 described above and illustrated in FIG. 1). FIGS. 2A to 2C also illustrate a structure 262, which may represent a housing or other structure of the GC unit 200 to which the FC 254 and microfluidic devices 256 and 258 are mounted, or a structure of a larger GC instrument such as a wall of the housing 142 described above and illustrated in FIG. 1. The location of the electronics 260 shown in FIG. 2A is by example only; the electronics 260 may generally be located anywhere on or in the GC unit 200 relative to the other components.

The GC column 252 may have any configuration now known or later developed. The GC column 252 typically includes a tube composed of metal, glass, or quartz that supports a stationary phase having an appropriate composition as appreciated by persons skilled in the art. As illustrated, a portion of the GC column 252 may be coiled to accommodate a desired length while minimizing the size of the GC unit 200. In some embodiments, the GC column 252 may be a low thermal mass (LTM) column such as, for example, a fused silica capillary. The GC column 252 may include a heating element such as, for example, a ceramic-insulated heating wire wound around the GC column 252, and may further include a locally positioned temperature sensor.

The FC 254 may generally have any configuration suitable for controlling the flow (e.g., mass flow rate and/or pressure) of input gases (carrier gas, or sample/carrier gas mixture) into the GC column 252. For such purposes, and depending on the particular embodiment, the FC 254 may include one or more ports (FC ports) for providing fluid communication with external devices, fluid conduits (tubes, channels, etc.) for defining flow paths, mass flow controllers (MFCs), pressure controllers (e.g., forward pressure controllers (FPCs), back pressure controllers (BPCs), etc.), flow restrictors, flow-switching valves for selecting flow paths, on/off valves, metering valves, flow meters, pressure transducers, tee-connections or unions for splitting or merging flow paths, etc., all of which components are generally understood by persons skilled in the art. In some embodiments, the FC 254 may be or include an electronic pneumatic controller (EPC) as appreciated by persons skilled in the art. The FC 254 may be reconfigurable to enable different implementations of the GC unit 200 as described further below.

The microfluidic devices 256 and 258 include respective bodies or chips 264 and 266 in which internal (or embedded) channels are formed to define fluid paths. The bodies 264 and 266 may have any shape such as, for example, rectilinear or prismatic (block, slab, plate, etc.), or disk-shaped. Each microfluidic device 256 and 258 includes two or more external ports. Such ports are "external" in the sense that they may be fluidly coupled to conduits or components external to the microfluidic devices 256 and 258. Each port communicates with at least one channel, and may communicate with one or more of the other ports via one or more channels. In some embodiments one or both microfluidic devices 256 and 258 include at least three ports, or at least four ports. At least some of the ports may be located on the same side of the body 264 or 266, or as illustrated the ports may be respectively located on different sides. At least some of the ports may be oriented in the same direction, or as illustrated the ports may be respectively oriented in different directions. In the illustrated embodiment, the inlet-side microfluidic device 256 includes a first port 268, a second port 270, a third port 272, and a fourth port 274 (FIGS. 2B and 2C). Likewise, the outlet-side microfluidic device 258 includes a first port 276, a second port 278, a third port 280, and a fourth port 282 (FIGS. 2B and 2C).

In the illustrated embodiment, the inlet-side first port 268 is fluidly coupled to the input end of the GC column 252 and the outlet-side first port 276 is fluidly coupled to the output end of the GC column 252. In this example, the inlet-side third port 272 may be fluidly coupled to an upstream GC component (e.g., the sample introduction system 104 of FIG. 1) to receive a flow of input gas (carrier gas, or sample/carrier gas mixture), which is then conducted into the GC column 252 via internal channels and the inlet-side first port 268. The outlet-side third port 280 may be fluidly coupled to a downstream GC component (e.g., the detector 112 of FIG. 1) to receive a flow of output gas (carrier gas, or sample/ carrier gas mixture containing chromatographically separated compounds) from the GC column 252 via internal channels and the outlet-side first port 276 and conduct the output gas to the downstream GC component. In various embodiments, the inlet-side second port 270 and/or inlet-side fourth port 274, and the outlet-side second port 276 and/or outlet-side fourth port 282, may be fluidly coupled to corresponding FC ports (not shown) as needed for enabling the FC 254 to control the gas flows through the inlet-side microfluidic device 256, the GC column 252, and the outlet-side microfluidic device 258.

Figure 3A:
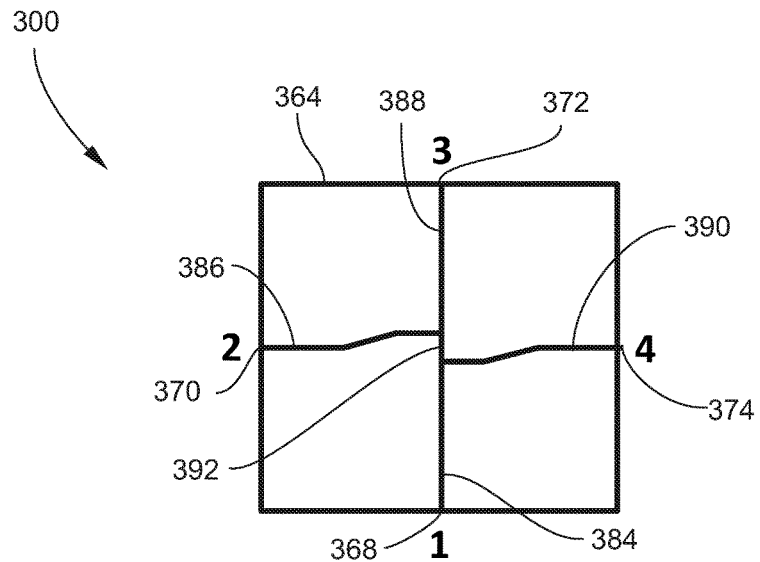
FIG. 3A is a schematic planarized view of an example of a microfluidic device showing internal channels according to some embodiments.

FIG. 3A is a schematic view of an example of a microfluidic device 300 according to some embodiments. The microfluidic device 300 may, for example, be representative of either or both of the microfluidic devices 256 and 258 just described. The microfluidic device 300 includes a body 364, a first port 368, a second port 370, a third port 372, and a fourth port 374. The microfluidic device 300 further includes a first channel 384, a second channel 386, a third channel 388, and a fourth channel 390 formed in the body 364. The first channel 384 communicates with the first port 368, the second channel 386 communicates with the second port 370, the third channel 388 communicates with the third port 372, and the fourth channel 390 communicates with the fourth port 374. Each channel communicates with at least one other channel at a junction or merge point between the two channels, such that each port communicates with at least one other port. In the illustrated embodiment, each channel (and corresponding port) nominally communicates with all other channels (and corresponding ports), but fluid flow and the direction of fluid flow in any channel may be controlled by controlling the pressure applied or seen at each port due to external components communicating with the ports. The length of each channel may be defined between its outside end (i.e., at the corresponding port at which the channel terminates) and its inside end (i.e., the point where the channel meets another channel). The lengths of all channels may be the same, or the length of at least one channel may be different from those of the other channels.

A junction at which two or more channels are adjoined may be a physically distinct feature such as a bend (resulting in a change in flow direction from one channel into another), a tee connection, or a cross connection. Alternatively, a junction may be more in the nature of a conceptual union between two channels such as, for example, a selected point that conceptually divides a channel into two shorter channels. In the illustrated embodiment, the microfluidic device 300 may be considered as including a common channel 392 that communicates with the inside ends of the first channel 384, second channel 386, third channel 388 and fourth channel 390. The common channel 392 has a distinct length between the inside ends of the second channel 386 and the fourth channel 390. Hence, the second channel 386 and the fourth channel 390 (or at least the portions of the second channel 386 and the fourth channel 390 that terminate at their respective inside ends) may be considered as being offset from each other in that at least their respective inside ends are spaced apart by a distance (i.e., the length of the common channel 392). This offset may be small, but large enough to facilitate the control of gas flow through the channels by way of different pressures at the ports. For example, assuming the first port 368 communicates with a GC column and the third port 372 communicates with an upstream sample input, an FC may provide carrier gas flows into the second port 370 and the fourth port 374 to control the sample flow rate into the GC column. In this manner, fluid flow into the GC column (through the third port 372) may be metered, pulsed, stopped, reversed, etc.

In terms of fluid flow paths, the ports and their corresponding channels (and particularly their inside ends) are arranged such that the second port 370 is between the first port 368 and the third port 372; the second port 370 is also between the third port 372 and the fourth port 374; the fourth port 374 is between the first port 368 and the second port 370; and the fourth port 374 is also between the first port 368 and the third port 372. Stated in another way, the channels are arranged such that the inside end of the second channel 386 is between the inside end of the first channel 384 and the inside end of the third channel 388; the inside end of the second channel 386 is also between the inside end of the third channel 388 and the inside end of the fourth channel 390; the inside end of the fourth channel 390 is between the inside end of the first channel 384 and the inside end of the second channel 386; the inside end of the fourth channel 390 is also between the inside end of the first channel 384 and the inside end of the third channel 388. This configuration may be taken into consideration when determining which ports are to be fluidly coupled to which external components in the process of building or configuring a GC unit utilizing the microfluidic device 300.

Figure 3B:
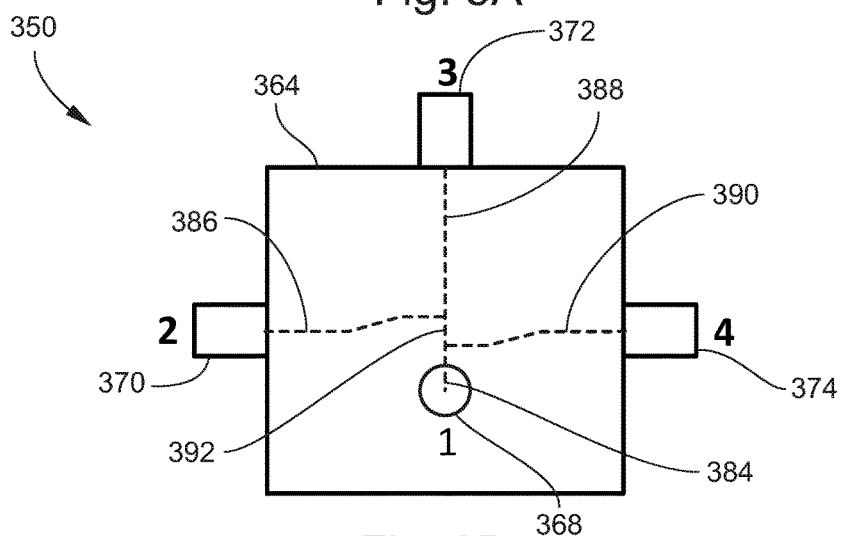
FIG. 3B is a schematic bottom plan view of an example of a microfluidic device according to some embodiments.

FIG. 3B is a schematic bottom plan view of an example of a microfluidic device 350 according to some embodiments. As in the case of the microfluidic devices 256 and 258 shown in FIGS. 2A to 2C, in the present embodiment the first port 368 and corresponding first channel 384 are oriented in a direction orthogonal to the plane in which the other ports 370, 372, and 374 and corresponding channels are oriented (from the perspective of FIG. 3B, the plane of the drawing sheet). At this plane, the first channel 384 may be considered as including a bend or terminating at a bend. FIG. 3B illustrates one example of implementing the flow paths and channel architecture shown in FIG. 3A. FIG. 3A may thus be considered as being a two-dimensional or planar diagram representative of any of the microfluidic devices shown in FIGS. 2A to 2C and 3B (or as a "planarized" version of such microfluidic devices), in which all flow paths into and out from the microfluidic device are conveniently shown.

Referring back to FIGS. 2A to 2C, the components of the GC unit 200 may be sized and arranged so as to minimize the total space occupied by the GC unit 200 and facilitate the use of a plurality of GC units 200 when building a GC device (e.g., the GC device 108 schematically illustrated in FIG. 1) having a desired configuration and functionality. FIGS. 2A to 2C illustrate one non-limiting example of a compact assembly, in which the FC 254 and microfluidic devices 256 and 258 are arranged in a linear array or series, with the FC 254 between the microfluidic devices 256 and 258 and the GC column 252 underneath the FC 254 and microfluidic devices 256 and 258.

A GC device may include a single GC unit 200 or more than one GC unit 200. For example, the GC device may include multiple GC units 200 with each GC unit 200 being fluidly coupled to at least one other GC unit 200. One or more of the GC units 200 constituting the GC device may be configured differently from the other GC units 200 in terms of the characteristics of their respective GC columns, how their respective FCs 254 are configured the type of components to which they are fluidly coupled, and/or what types of fluid connections are made at the ports of their respective microfluidic devices 256 and 258. Non-limiting examples of various embodiments (or architectures) of GC devices built from different arrangements or clusters of GC units 200 are described below.

Figure 4:
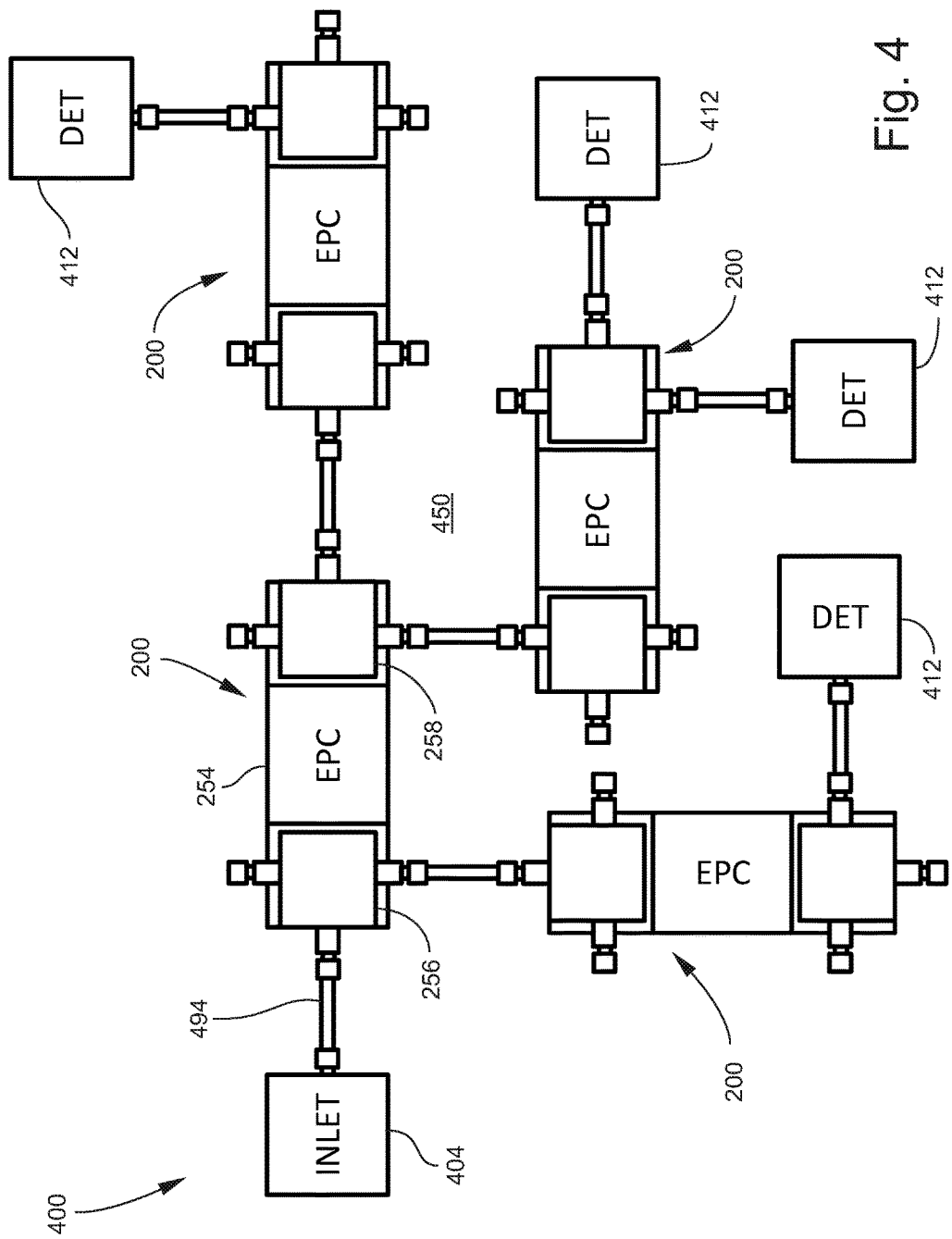
FIG. 4 is a schematic view of an example of a GC system (or a portion thereof) according to some embodiments.

FIG. 4 is a schematic view of an example of a GC system 400 (or a portion thereof) according to some embodiments, demonstrating how a highly scalable and configurable GC architecture may be achieved in accordance with the present disclosure. The GC system 400 includes a GC device 450 communicating with a sample inlet 404 and a plurality of detectors 412. The sample inlet 404 may be or be part of a sample introduction system such as described above in conjunction with FIG. 1. The GC system 400 may include more than one sample inlet 404 for a purpose such as merging different sample flows. The detectors 412 may be all of the same type, or at least one detector 412 may be different than the other detectors 412. In this embodiment, the GC device 450 includes a plurality of GC units 200. Each GC unit 200 may be configured as described above and illustrated in FIGS. 2A to 2C, thus including a GC column (not shown), an FC 254, an inlet-side (or first) microfluidic device 256, and an outlet-side (or second) microfluidic device 258. Each microfluidic device 256 and 258 of each GC unit 200 is fluidly coupled to at least one component external to that GC unit 200, such as one or more sample inlets 404, detectors 412, and/or other GC units 200. For example, fluid communication between the ports of separate components may be implemented by transfer lines 494 (e.g., conduits, tubes, etc.) appropriately coupled to such ports. Depending on the embodiment, a transfer line 494 may function as a sample loop for a purpose such as temporarily holding a desired quantity of sample material. For simplicity, fluid connections between the FCs 254 and corresponding microfluidic devices 256 and 258 are not shown in FIG. 4.

FIG. 4 illustrates the ease with which the GC device 450 may be configured according to any desired architecture, by determining the number and different types of GC units 200 to be included and how the GC units 200 are to be arranged and fluidly coupled relative to each other and to components external to the GC device 450. As described above, different GC units 200 may provide different functionalities through selection of their respective GC columns and configuration of their respective FCs 254, by coupling them to different combinations of fluidic components. Although different GC units 200 may function differently, the microfluidic devices 256 and 258 of each GC unit 200 may all have the same configuration. In such case, the microfluidic devices 256 and 258 disclosed herein may be characterized as being universal devices. By designing an appropriate combination and arrangement of GC units 200, the GC device 450 may be configured to implement a very wide variety of GC operational modes now known or later developed, including multidimensional GC modes.

A non-exhaustive number of embodiments of GC units and associated GC devices and systems will now be described in conjunction with FIGS. 5 to 15. These embodiments may be described or represented at least in part through the use of a notation developed by the inventor, presented in the TABLE below. In the TABLE, the "Element" column indicates the symbol utilized to represent a particular type of device or component. The "Bonds" column indicates the number of bonds, or fluid flow paths or fluidic connections (by way of ports, transfer lines, etc.), with which the corresponding element may communicate, in typical embodiments disclosed herein. The "Chromatographic" column indicates whether the corresponding element may contribute to chromatographic separation. The "Resistive" column indicates whether the corresponding element may provide fluid flow resistance. The "Description" column provides a brief description of the corresponding element.

TABLE

| Element | Bonds | Chromatographic | Resistive | Description |
|---|---|---|---|---|
| I | 1 | yes | no | inlet/sampler without split |
| J | 1 | yes | no | inlet/sampler with split |
| D | 1 | yes | yes/no | detector |
| M | 1 | no | no | MFC |
| F | 1 | no | no | FPC |
| B | 1 | yes | no | BPC |
| R | 2 | yes/no | yes | restrictor |
| A | 2 | yes | yes | thermal modulator |
| T | 3 | no | no | pneumatic tee connector |
| S | 3 | no | no | switch valve |
| X—C—X | 6 | yes | yes | microfluidic device |

In the above TABLE, various elements may be fluidly coupled together by "fluidic bonds" to produce a diagram or formula, which may be presented in a manner analogous to a molecular formula. A single bond is represented by the minus symbol "–" and a double bond is represented by the equals symbol "=". A formula may be representative of a GC unit or functional template which, when fluidly coupled to one or more other elements, GC units, or templates, results in a GC system. For example, in the last row of the above TABLE, the template "X–C–X" represents a microfluidic device comprising a column "C" fluidly coupled between two individual microfluidic devices each designated by "X" (e.g., an inlet-side microfluidic device and outlet-side microfluidic device). As another example, the formula for a GC unit such as illustrated in FIGS. 2A to 2C may be presented as "–X=T–MF–T=X–" (see also FIG. 5) or "–X=T–MB–T=X–", depending on whether the pressure controller of the FC functions as an FPC ("F") or a BPC ("B"). When specifying a GC unit, the column "C" and its bonds to the microfluidic devices X may be omitted for brevity and simplification. A formula may also be representative of an entire GC system (e.g., from sample inlet to detector), examples of which are described below.

Figure 5:
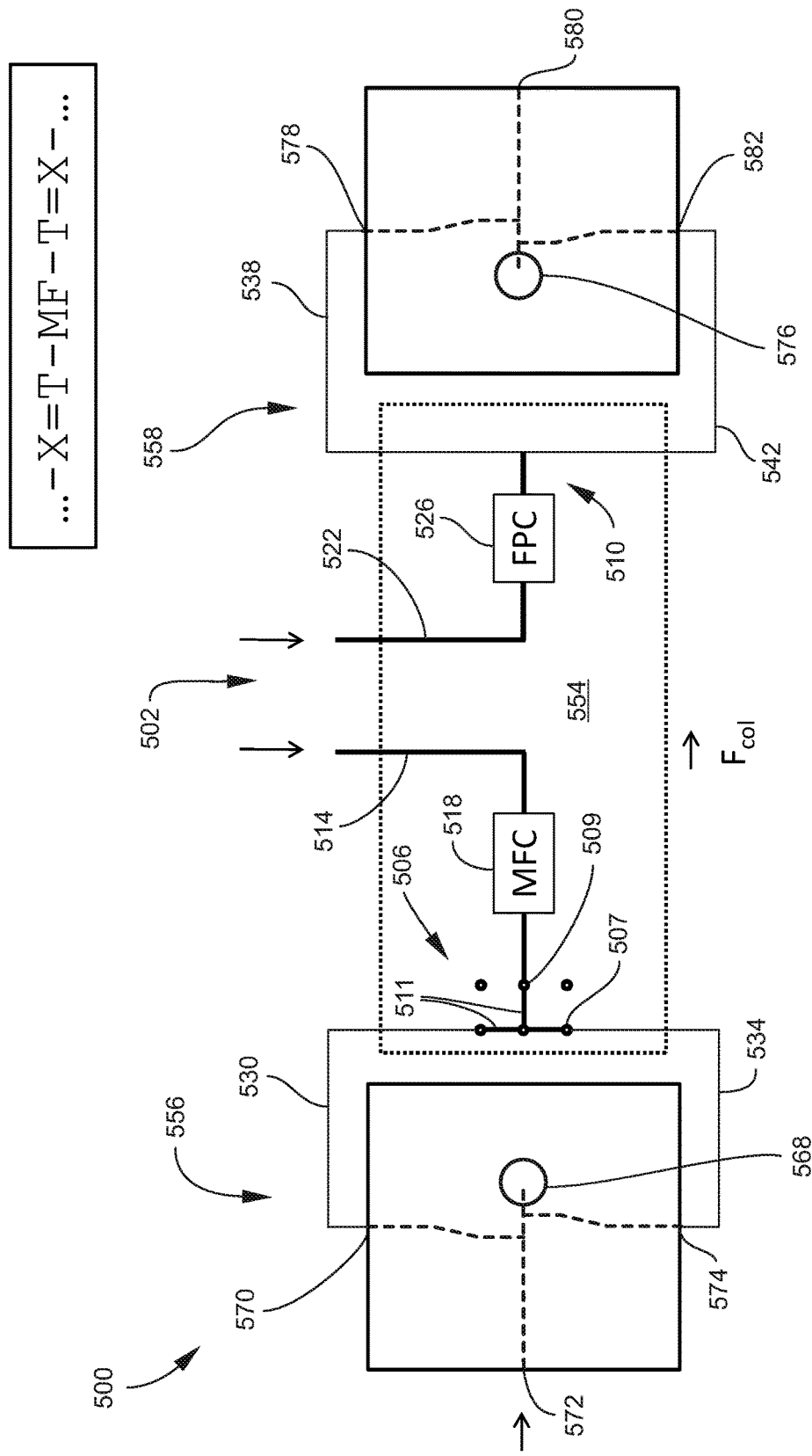
FIG. 5 is a schematic view of an example of a GC unit (or a GC device including the GC unit) according to some embodiments.

FIG. 5 is a schematic view of an example of a GC unit 500 (or a GC device including the GC unit 500) according to some embodiments. FIG. 5 also includes a diagram of the GC unit 500 using the notation presented in the TABLE above. The GC unit 500 may generally include a GC column (not shown), an FC 554, an inlet-side (or first) microfluidic device 556 and an outlet-side (or second) microfluidic device 558. The inlet-side microfluidic device 556 includes a first port 568, a second port 570, a third port 572, a fourth port 574, and associated internal channels as described above. Likewise, the outlet-side microfluidic device 558 includes a first port 576, a second port 578, a third port 580, a fourth port 582, and associated internal channels as described above. In the present embodiment, the inlet-side first port 568 is fluidly coupled to the input end of the GC column and the outlet-side first port 576 is fluidly coupled to the output end of the GC column. The inlet-side third port 572 may be fluidly coupled to an upstream GC component to receive a flow of input gas (carrier gas, or sample/carrier gas mixture). The input gas is then conducted into the GC column via the internal channels and the inlet-side first port 568. The outlet-side third port 580 may be fluidly coupled to a downstream GC component to receive a flow of output gas (carrier gas, or sample/carrier gas mixture containing chromatographically separated compounds) $F_{COL}$ from the GC column via the outlet-side first port 576 and internal channels, and conduct the output gas to the downstream GC component.

In the present embodiment, the FC 554 includes an FC input port 502 for receiving a flow of carrier gas, a first FC output port 506 communicating with the inlet-side microfluidic device 556, and a second FC output port 510 communicating with the outlet-side microfluidic device 558. The FC 554 also includes a first carrier gas line 514 for conducting a first carrier gas flow from the FC input port 502 to the first FC output port 506, an MFC 518 operatively coupled to the first carrier gas line 514 for controlling the first carrier gas flow, a second carrier gas line 522 for conducting a second carrier gas flow from the FC input port 502 to the second FC output port 510, and an FPC 526 for controlling the second carrier gas flow. The FC input port 502 may be a single port followed by a flow splitter (e.g., a tee-connection with the first carrier gas line 514 and second carrier gas line 522) that splits an incoming carrier gas flow into the first and second carrier gas flows. Alternatively, the FC input port 502 may include two ports respectively communicating with the first carrier gas line 514 and second carrier gas line 522.

In some embodiments, the first FC output port 506 and/or the second FC output port 510 are reconfigurable fluidic components. FIG. 5 illustrates an example of the first FC output port 506 as a reconfigurable component. The first FC output port 506 may be configured by the user to provide one or more output paths, flow restrictors, flow switching valves, etc. For this purpose, the first FC output port 506 may include one or more individual external ports 507, internal ports 509, and conduits 511. Ports not being utilized to define flow paths in a particular embodiment may be blocked or isolated from active flow paths by any suitable means. The conduits 511 may include pre-existing channels between certain ports that are blocked when not in use, and/or small lengths of conduits (e.g., tubes) that are removably coupled between selected ports. A conduit may be provided to serve as part of a flow path or additionally to serve as a flow restrictor. Other fluidic components such as switch valves (not shown) may also be made available for coupling to selected ports. In the illustrated example, the first FC output port 506 has been configured as a tee-connection by coupling the first carrier gas line 514 with one of the internal ports 509 and utilizing conduits 511 to direct the flow from the internal port 509 to two output ports 507. The output ports 507 are in turn respectively coupled to the inlet-side second port 570 and the inlet-side fourth port 574 via respective inlet-side carrier gas lines 530 and 534.

Also in this embodiment, the second FC output port 510 includes a tee-connection communicating with the second carrier gas line 522. Output ports of the tee-connection are in turn respectively coupled to the outlet-side second port 576 and the outlet-side fourth port 582 via respective outlet-side carrier gas lines 538 and 542. The second FC output port 510 may or may not be reconfigurable.

In the present embodiment, the GC unit 500 thus is configured such that the column flow $F_{COL}$ is controlled by the local FPC-controlled flow through the second carrier gas line 522, and may also be controlled by an upstream device fluidly coupled to the inlet-side third port 572.

Figure 6:
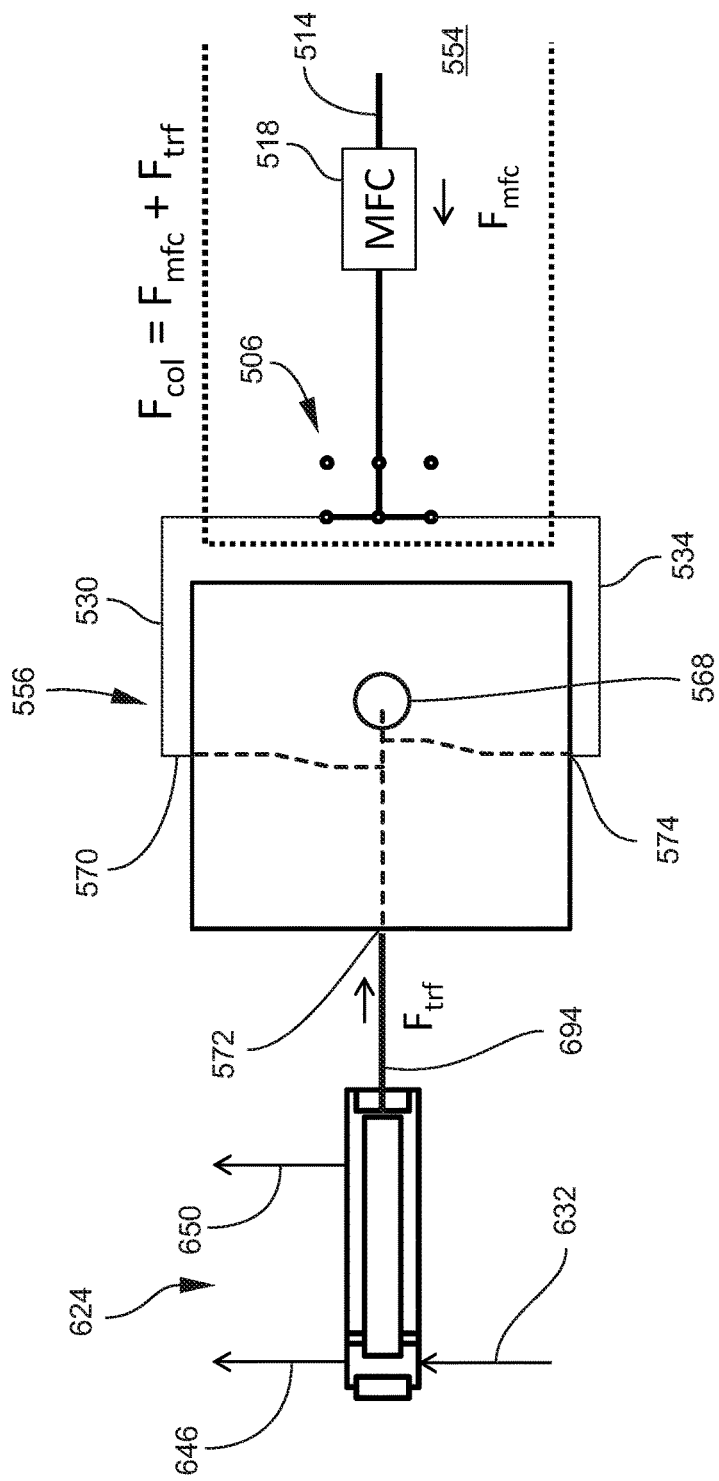
FIG. 6 is a schematic view of the inlet side of the GC unit illustrated in FIG. 5 coupled to a GC inlet according to some embodiments.

FIG. 6 is a schematic view of the inlet side of the GC unit 500 with the inlet-side third port 572 fluidly coupled to a GC inlet 624 via a transfer line 694. FIG. 6 also includes a diagram of a more complete GC unit 500 and an example of an associated GC system of which the GC unit 500 may form a part, using the notation presented in the TABLE above. As an example, the GC inlet 624 is illustrated as a S/SL inlet of known design that includes a sample/carrier gas mixing chamber between a septum and a liner, a carrier gas supply line 632 communicating with the mixing chamber, a septum purge vent 646 communicating with the mixing chamber, and a split flow vent 650 communicating with a split flow chamber surrounding the liner, and a temperature control device (not shown) for controlling the temperature of the input gas (carrier gas, or sample/carrier gas mixture). The transfer line 694 provides a flow of input gas $F_{TRF}$ into the inlet-side microfluidic device 556. As shown in the diagram, the outlet side of the GC unit 500 may communicate with a detector.

With the GC unit 500 configured as just described, the GC inlet 624 controls the GC unit head pressure and hence the total column flow $F_{COL}$. Moreover, the MFC-controlled flow $F_{MFC}$ through the carrier gas lines 530 and 534 contributes to the total column flow $F_{COL}$ as follows: $F_{COL}=F_{MFC}+F_{TRF}$. Sample injection may be metered by setting $F_{MFC}<F_{COL}$ and varying $F_{MFC}$ as needed to obtain a desired or programmed sample flow rate $F_{TRF}$. Sample injection may be timed or pulsed by switching the setting for $F_{MFC}$ between $F_{MFC}<F_{COL}$ and $F_{MFC}>F_{COL}$ at desired or programmed intervals of time. Metered injection allows the use of a smaller sample amount in an analysis, without wasting a large split flow at the GC inlet 624. Timed injection also allows the use of a smaller sample amount, and additionally provides a narrow band of injected analytes.

Figure 7:
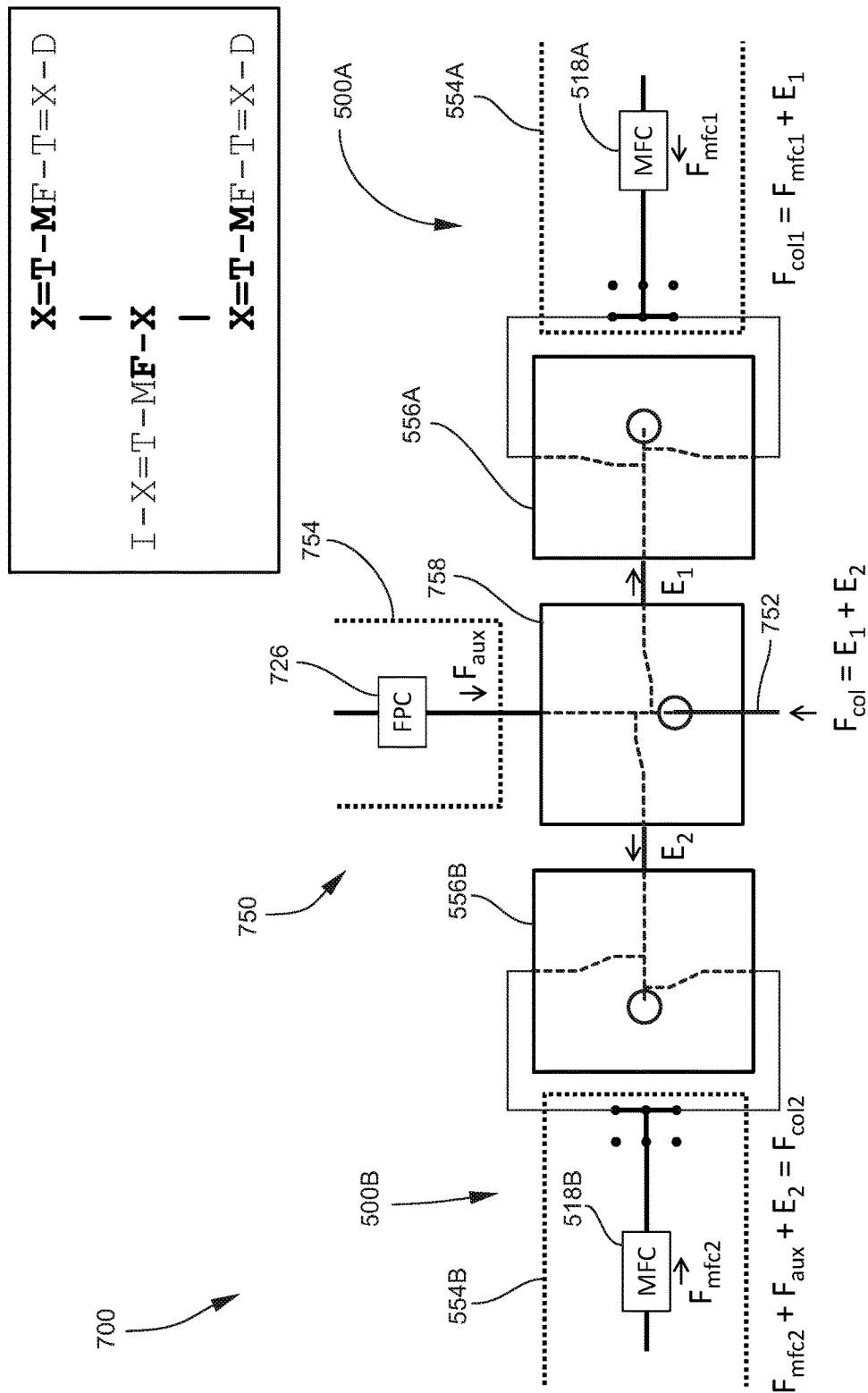
FIG. 7 is a schematic view of an example of a GC device (or a portion thereof) according to another embodiment.

FIG. 7 is a schematic view of an example of a GC device 700 (or a portion thereof) according to another embodiment. The GC device 700 includes multiple GC units fluidly coupled together. Specifically, the GC device 700 includes at least a first GC unit 500A, a second GC unit 500B, and a third GC unit 750. For simplicity, FIG. 7 illustrates only the inlet sides of the first GC unit 500A and second GC unit 500B and only the outlet side of the third GC unit 750. However, FIG. 7 also includes a diagram of an example of a more complete GC device 700 and associated GC system using the notation presented in the TABLE above. The GC units 500A, 500B, and 750 may generally be configured the same as or similar to GC units described above. Thus, as shown or partially shown in FIG. 7, the first GC unit 500A includes a first FC 554A that includes a first MFC 518A, and a first inlet-side microfluidic device 556A; the second GC unit 500B includes a second FC 554B that includes a second MFC 518B, and a second inlet-side microfluidic device 556B; and the third GC unit 750 includes a third FC 754 that includes a (third) FPC 726, and a (third) outlet-side microfluidic device 758. FIG. 7 also shows a portion of a third GC column 752 of the third GC unit 750. For simplicity, the respective first and second GC columns of the first GC unit 500A and second GC unit 500B are not shown.

In the present embodiment, the third GC unit 750 is positioned as an upstream unit that that may receive sample injections, as shown in the diagram. The first GC unit 500A and second GC unit 500B are positioned as downstream units, and are fluidly coupled to the third GC unit 750 so as to be able to receive the effluent from the third GC column 752. As shown in the diagram, the first GC unit 500A and second GC unit 500B may communicate with respective first and second detectors. The GC device 700 is configured for implementing two modes of operation, effluent splitting and effluent switching, and for switching between these two modes of operation. Activation/deactivation of, and switching between, the two modes may be selectable or programmable by the user through hardware—and/or software-based control of the GC device 700 as appreciated by persons skilled in the art.

As one non-limiting example of configuring the GC device 700 for implementing the two modes, the GC columns are fluidly coupled to the inlet-side and outlet side first ports of the respective GC units 500A, 500B, and 750 as described above (e.g., FIG. 2A). The first MFC 518A and second MFC 518B are fluidly coupled to the second and fourth ports of the respective first inlet-side microfluidic device 556A and second inlet-side microfluidic device 556B as described above (e.g., FIG. 5). The outlet-side microfluidic device 758 of the third GC unit 750 is positioned such that the FPC 726 of the third GC unit 750 communicates with the third port of the outlet-side microfluidic device 758, thereby providing an auxiliary carrier gas flow $F_{AUX}$. The fourth port of the outlet-side microfluidic device 758 communicates with the third port of the first inlet-side microfluidic device 556A to provide a first (split) effluent flow $E_1$ to the first GC unit 500A. The second port of the outlet-side microfluidic device 758 communicates with the third port of the second inlet-side microfluidic device 556B to provide a second (split) effluent flow $E_2$ to the second GC unit 500B.

In the present embodiment, the FPC 726 of the third GC unit 750 enables the effluent from the third GC column 752 (third column flow $F_{COL}$) to be split into two separate effluent flows $E_1$ and $E_2$. Hence, the third column flow $F_{COL}=E_1+E_2$. The FPC 726 also controls the total flow rates through the first and second GC columns, $F_{COL1}$ and $F_{COL2}$. The first column flow $F_{COL1}=F_{MFC1}+E_1$, where $F_{MFC1}$ is the carrier gas flow through the first MFC 518A. The second column flow $F_{COL2}=F_{MFC2}+F_{AUX}+E_2$, where $F_{MFC2}$ is the carrier gas flow through the second MFC 518B. With the outlet-side microfluidic device 758 oriented as shown in FIG. 7, the offset between the internal ends of the channels leading to the second and fourth ports of the outlet-side microfluidic device 758 (as described above in conjunction with FIG. 3A) ensures that the entire auxiliary carrier gas flow $F_{AUX}$ is directed into the second GC unit 500B under normal operating conditions.

By the configuration just described, effluent splitting is implemented by setting the flow rates $F_{MFC1}$ and $F_{MFC2}$ as needed to obtain a desired split ratio $E_1:E_2$. The other mode, effluent switching, entails switching the entire effluent flow $F_{COL}$ from the third GC column 752 to the first GC column (first GC unit 500A) or to the second GC column (second GC unit 500B). To switch the entire effluent to the first GC column, $F_{COL}$ is set to be less than $F_{COL1}$ ($F_{COL}<F_{COL1}$), which may be done by controlling the setting of the FPC 726, and $F_{MFC1}$ is set to be less than the difference between $F_{COL1}$ and $F_{COL}$ ($F_{MFC1}<F_{COL1}-F_{COL}$). To switch the entire effluent to the second GC column, $F_{MFC2}$ is set to a small value, and $F_{MFC1}$ is set to be greater than $F_{COL1}$ ($F_{MFC1}>F_{COL1}$). The GC device 700 is thus useful for selectively switching or splitting sample flows among different downstream components such as GC columns and associated detectors. It will be noted that the flow into any downstream GC unit may be further split at its own inlet-side microfluidic device to an additional GC unit, detector, or other fluidic component. Such flow splitting may be continued in as many iterations as desired.

Figure 8:
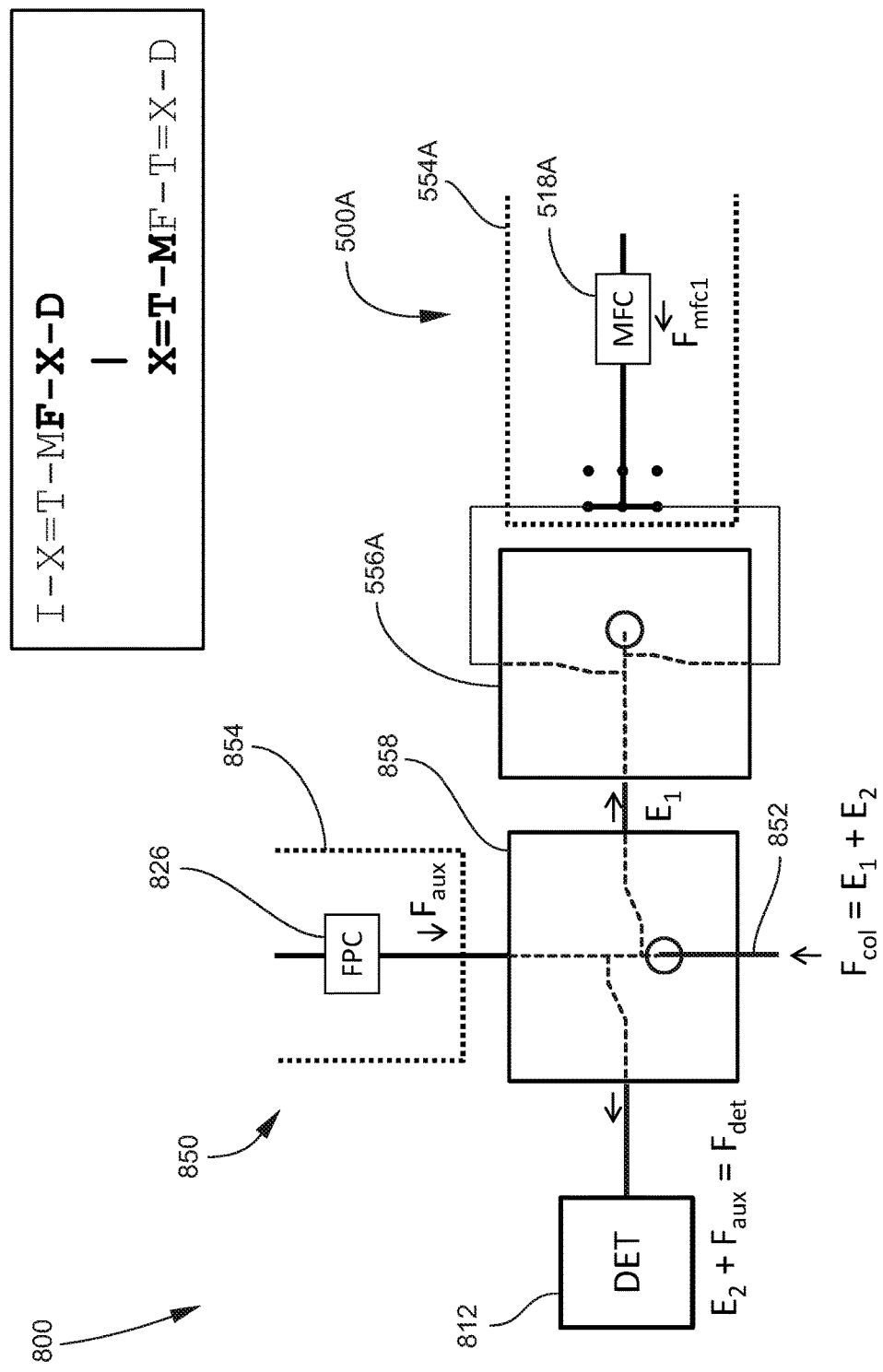
FIG. 8 is a schematic view of an example of a GC device (or a portion thereof) according to another embodiment.

FIG. 8 is a schematic view of an example of a GC device 800 (or a portion thereof) according to another embodiment. The GC device 800 includes at least a first GC unit 500A and a second GC unit 850. For simplicity, FIG. 8 illustrates only the inlet side of the first GC unit 500A and only the outlet side of the second GC unit 850. However, FIG. 8 also includes a diagram of an example of a more complete GC device 800 and associated GC system using the notation presented in the TABLE above. The first GC unit 500A and the second GC unit 850 may generally be configured the same as or similar to the first GC unit 500A and the third GC unit 850 described above in conjunction with FIG. 7. Thus, as shown or partially shown in FIG. 8, the first GC unit 500A includes a first FC 554A that includes a first MFC 518A, and a first inlet-side microfluidic device 556A; and the second GC unit 850 includes a second FC 854 that includes a (second) FPC 826, and a (second) outlet-side microfluidic device 858. FIG. 8 also shows a portion of a second GC column 852 of the second GC unit 850. For simplicity, the first GC column of the first GC unit 500A is not shown.

In the present embodiment, the second GC unit 850 is positioned as an upstream unit that receives sample injections, as shown in the diagram. The first GC unit 500A and a (second) detector 812 are positioned as downstream units, and are fluidly coupled to the second GC unit 850 so as to be able to receive the effluent from the second GC column 852. As shown in the diagram, another (first) detector may be positioned downstream from the first GC column of the first GC unit 500A. The GC device 800 is configured for implementing, and for switching between, effluent splitting and effluent switching modes of operation.

As one non-limiting example of configuring the GC device 800 for implementing the two modes, the GC columns are fluidly coupled to the inlet-side and outlet side first ports of the respective GC units 500A and 850 as described above (e.g., FIG. 2A). The first MFC 518A is fluidly coupled to the second and fourth ports of the first inlet-side microfluidic device 556A as described above (e.g., FIG. 5). The outlet-side microfluidic device 858 of the second GC unit 850 is positioned such that the FPC 826 of the second GC unit 850 communicates with the third port of the outlet-side microfluidic device 858, thereby providing an auxiliary carrier gas flow $F_{AUX}$ as in the case of the embodiment illustrated in FIG. 7. The fourth port of the outlet-side microfluidic device 858 communicates with the third port of the first inlet-side microfluidic device 556A to provide a first (split) effluent flow $E_1$ to the first GC unit 500A, and ultimately to the first detector downstream from first GC unit 500A. The second port of the outlet-side microfluidic device 858 communicates directly with the second detector 812 to provide a second (split) effluent flow $E_2$ to the second detector 812. The GC device 800 thus may be configured similarly to the GC device 700, but without a GC column between the second outlet-side microfluidic device 858 and the second detector 812.

In the present embodiment, the FPC 826 of the second GC unit 850 enables the effluent from the second GC column 852 (second column flow $F_{COL}$) to be split into two separate effluent flows $E_1$ and $E_2$. Hence, the second column flow $F_{COL}=E_1+E_2$. The FPC 826 also controls the total flow rate through the first GC column, $F_{COL1}$. The first column flow $F_{COL1}=F_{MFC1}+E_1$, where $F_{MFC1}$ is the carrier gas flow through the first MFC 518A. The second detector 812 receives a total output flow $F_{DET}=F_{AUX}+E_2$. The outlet-side microfluidic device 858 is oriented in the same manner as the outlet-side microfluidic device 758 shown in FIG. 7, thus ensuring that the entire auxiliary carrier gas flow $F_{AUX}$ is directed into the second detector 812 under normal operating conditions.

By the configuration just described, effluent splitting is implemented by setting the flow rate $F_{MFC1}$ as needed to obtain a desired split ratio $E_1:E_2$. In the effluent switching mode, to switch the entire effluent to the first GC column, $F_{COL}$ is set to be less than $F_{COL}(F_{COL}<F_{COL1})$, and $F_{MFC1}$ is set to be less than the difference between $F_{COL1}$ and $F_{COL}$ ($F_{MFC1}<F_{COL1}-F_{COL}$). To switch the entire effluent to the second detector 812, $F_{MFC1}$ is set to be greater than $F_{COL}$ ($F_{MFC1}>F_{COL1}$).

It can be seen that the GC device 800 may be utilized for multidimensional two-dimensional GC (MD-2DGC) operations in which the (second) detector 812 monitors the effluent from the first dimension (the upstream (second) GC column 852 in the present embodiment), and heart-cuts are switched to the second dimension (the downstream GC column of the first GC unit 500A in the present embodiment) for additional compound separation. In the present embodiment, neither a switch valve nor a Deans switch is required for such operation.

Figure 9:
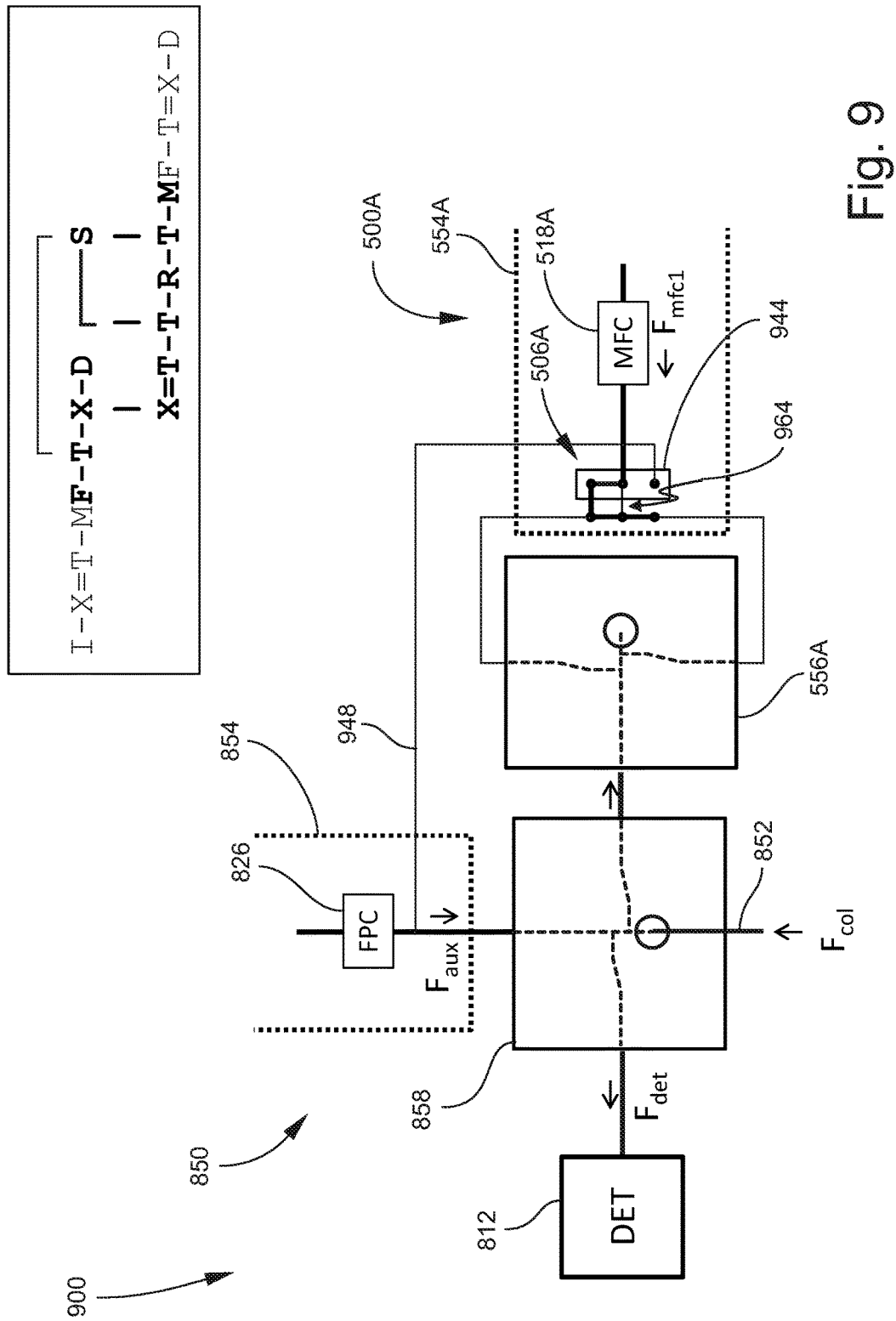
FIG. 9 is a schematic view of an example of a GC device (or a portion thereof) according to another embodiment.

FIG. 9 is a schematic view of an example of a GC device 900 (or a portion thereof) according to another embodiment. The GC device 900 includes at least a first GC unit 500A and a second GC unit 850. For simplicity, FIG. 9 illustrates only the inlet side of the first GC unit 500A and only the outlet side of the second GC unit 850. However, FIG. 9 also includes a diagram of an example of a more complete GC device 900 and associated GC system using the notation presented in the TABLE above. The first GC unit 500A and the second GC unit 850 may generally be configured similar to the first GC unit 500A and the second GC unit 850 described above in conjunction with FIG. 8. Thus, the second GC unit 850 is positioned as an upstream unit that receives sample injections, as shown in the diagram. The first GC unit 500A and a (second) detector 812 are positioned as downstream units, and are fluidly coupled to the second GC unit 850 so as to be able to receive the effluent from a second GC column 852. As shown in the diagram, another (first) detector may be positioned downstream from the first GC column of the first GC unit 500A.

The GC device 900 is configured for implementing, and for switching between, effluent splitting and effluent switching modes of operation, in a manner analogous to the GC device 800 described above in conjunction with FIG. 8. The GC device 900 is further configured for a heart-cut mode of operation. As one non-limiting example of configuring the GC device 900 for implementing heart-cutting, the first FC output port 506 has been configured to include a switch valve 944 between the first MFC 518A and the tee-connector that communicates with the second and fourth ports of the first inlet-side microfluidic device 556A. The switch valve 944 is movable between a first position and a second position. At the first position, illustrated in FIG. 9, the switch valve 944 directs carrier gas from the first MFC 518A to the tee-connector and hence to the first inlet-side microfluidic device 556A in the manner described above (see, e.g., FIG. 8). At the first position, $F_{MFC}$ may be set so as to block the flow of effluent into the first GC column associated with the first GC unit 500A. At the second position, the switch valve 944 directs the carrier gas from the first MFC 518A through a bypass line 948 and to the second GC unit 850. The bypass line 948 is fluidly coupled between a port of the first FC output port 506 and a tee-connector positioned downstream of the FPC 826 of the second GC unit 850, either at the second FC 854 or between the second FC 854 and the outlet-side microfluidic device 858. Thus, at the second position, the MFC-controlled carrier gas flow $F_{MFC1}$ from the first GC unit 500A is combined with the FPC-controlled carrier gas flow $F_{AUX}$ from the second GC unit 850. At the second position, the combined carrier gas flow may sweep the effluent flow from the second GC column 852 into the first GC column associated with the first GC unit 500A. A flow restrictor 964 is fluidly coupled between the center port receiving the carrier gas flow from the first MFC 518A and a center port of the tee-connector of the first FC output port 506 to maintain a trickle flow to the second and fourth ports of the first inlet-side microfluidic device 556A while the bypass line 948 is active (i.e., while the switch valve 944 is in the second position).

In the present embodiment, the FPC 826 controls the total flow rate through the first GC column, $F_{COL1}$, and the total flow rate into the second detector 812, $F_{DET}$. The GC device 900 may be useful for MD-2DGC applications requiring fast flow switching, such as where it is desired that the heart-cut windows be very short or that heart-cut windows be repeated at a high frequency.

Figure 10:
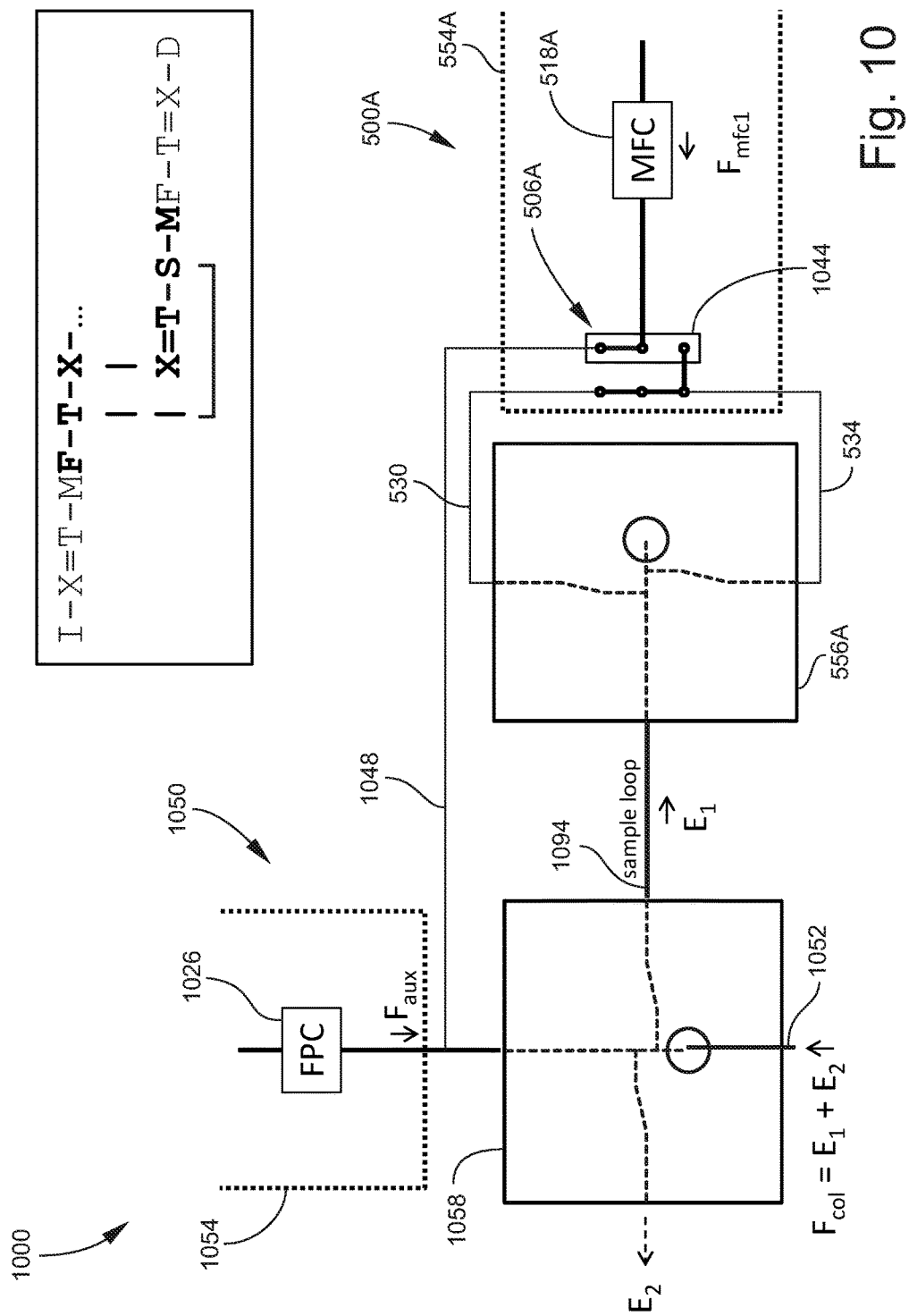
FIG. 10 is a schematic view of an example of a GC device (or a portion thereof) according to another embodiment.

FIG. 10 is a schematic view of an example of a GC device 1000 (or a portion thereof) according to another embodiment. The GC device 1000 includes at least a first GC unit 500A and a second GC unit 1050. For simplicity, FIG. 10 illustrates only the inlet side of the first GC unit 500A and only the outlet side of the second GC unit 1050. However, FIG. 10 also includes a diagram of an example of a more complete GC device 1000 and associated GC system using the notation presented in the TABLE above. As shown or partially shown in FIG. 10, the first GC unit 500A includes a first FC 554A that includes a first MFC 518A, and a first inlet-side microfluidic device 556A; and the second GC unit 1050 includes a second FC 1054 that includes a (second) FPC 1026, and a (second) outlet-side microfluidic device 1058. FIG. 10 also shows a portion of a second GC column 1052 of the second GC unit 1050. For simplicity, the first GC column of the first GC unit 500A is not shown.

In the present embodiment, the second GC unit 1050 is positioned as an upstream unit that receives sample injections, as shown in the diagram. The first GC unit 500A is positioned as a downstream unit, and is fluidly coupled to the second GC unit 1050 so as to be able to receive the effluent from the second GC column 1052. As shown in the diagram, the first GC unit 500A may communicate with a detector. Another GC unit, or other type of fluid-receiving component, may be fluidly coupled (not shown) to the second GC unit 1050 so as to be able to receive the effluent from the second GC column 1052.

The GC device 1000 is configured for implementing GC×GC flow modulation, by which a sample loop 1094 may be alternately filled with effluent from the first dimension (second GC column 1052) and flushed to flow the effluent into the second dimension (GC column of first GC unit 500A). As one non-limiting example of configuring the GC device 1000 for implementing this mode, the GC columns are fluidly coupled to the inlet-side and outlet side first ports of the respective GC units 500A and 1050 as described above (e.g., FIG. 2A). The first MFC 518A is fluidly coupled to the second and fourth ports of the first inlet-side microfluidic device 556A as described above (e.g., FIG. 5), but in the present embodiment this coupling is selectable as described below. The second outlet-side microfluidic device 1058 is positioned such that the second FPC 1026 communicates with the third port of the second outlet-side microfluidic device 1058, thereby providing an auxiliary carrier gas flow $F_{AUX}$. The second outlet-side microfluidic device 1058 is oriented such that its second port communicates with the third port of the first inlet-side microfluidic device 556A via the sample loop 1094, i.e., a transfer line having dimensions suitable for containing a desired amount of fluid at a desired point of time. The second outlet-side microfluidic device 1058 is oriented to provide at least a first (split) effluent flow $E_1$ from the second GC column 1052 to the first GC unit 500A, and ultimately to the first detector downstream from the first GC unit 500A. The orientation of the second outlet-side microfluidic device 1058 also ensures that that the entire auxiliary carrier gas flow $F_{AUX}$ is directed into the sample loop 1094 under normal operating conditions. The second port of the second outlet-side microfluidic device 1058 may provide a second (split) effluent flow $E_2$ to another GC unit or other type of fluid-receiving component (not shown).

Also in the present embodiment, the first FC output port 506A has been configured to include a switch valve 1044 between the first MFC 518A and the tee-connector that communicates with the second and fourth ports of the first inlet-side microfluidic device 556A. The switch valve 1044 is movable between a first position and a second position. At the first position, the switch valve 1044 directs carrier gas from the first MFC 518A to the tee-connector and hence to the first inlet-side microfluidic device 556A as described above. At the second position, illustrated in FIG. 10, the switch valve 1044 directs the carrier gas from the first MFC 518A through a bypass line 1048 and to the second GC unit 1050. The bypass line 1048 is fluidly coupled between a port of the first FC output port 506A and a tee-connector positioned downstream of the second FPC 1026, either in the second FC 1054 or between the second FC 1054 and the second outlet-side microfluidic device 1058. Thus, at the second position, the MFC-controlled carrier gas flow $F_{MFC1}$ from the first GC unit 500A is combined with the FPC-controlled carrier gas flow $F_{AUX}$ from the second GC unit 850. Thus, the first position may be utilized for filling the sample loop 1094 by blocking flow into the first GC column, and the second position may be utilized for flushing the sample loop 1094 with the aid of a relatively high carrier gas flow through the bypass line 1048.

It will be noted that the GC device 1000 is capable of effluent splitting or switching to a second downstream fluidic component (not shown) fluidly coupled to the fourth port of the second GC unit 1050, such that MD-2DGC may be carried out simultaneously with GC×GC flow modulation. In this case, the fluid coupling between the second downstream fluidic component and the fourth port of the second GC unit 1050 should have a negligible flow resistance under the typical high flush flow of GC×GC flow modulation to enable the second FPC 1026 to effectively control the head pressure of the downstream (first) GC unit 500A and hence $F_{COL1}$.

Figure 11:
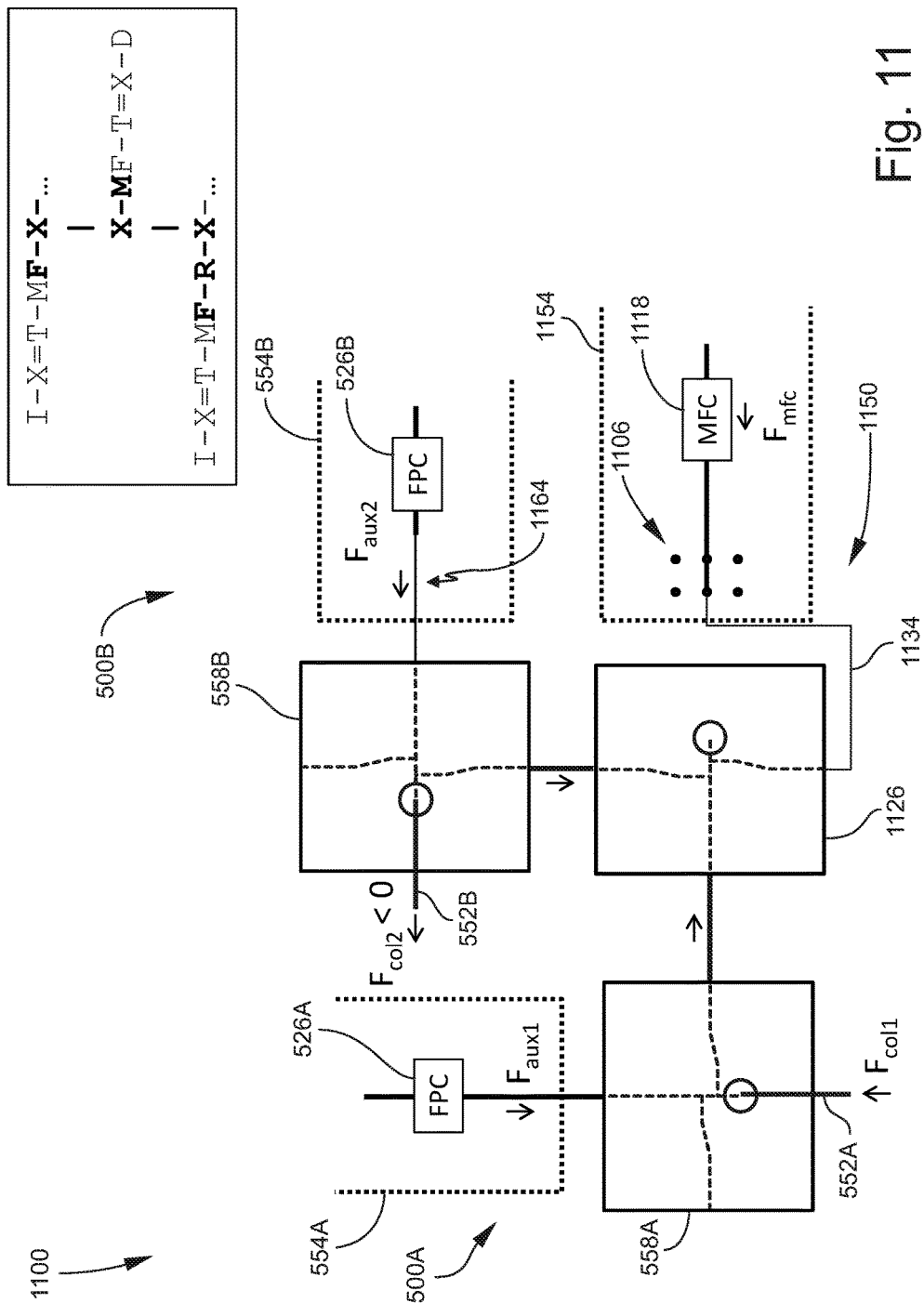
FIG. 11 is a schematic view of an example of a GC device (or a portion thereof) according to another embodiment.

FIG. 11 is a schematic view of an example of a GC device 1100 (or a portion thereof) according to another embodiment. The GC device 1100 includes at least a first GC unit 500A, a second GC unit 500B, and a third GC unit 1150. For simplicity, FIG. 11 illustrates only the outlet inlet sides of the first GC unit 500A and second GC unit 500B and only the inlet side of the third GC unit 750. However, FIG. 11 also includes a diagram of an example of a more complete GC device 1100 and associated GC system using the notation presented in the TABLE above. As shown or partially shown in FIG. 7, the first GC unit 500A includes a first FC 554A that includes a first FPC 526A, and a first outlet-side microfluidic device 558A; the second GC unit 500B includes a second FC 554B that includes a second FPC 526B, and a second outlet-side microfluidic device 558B; and the third GC unit 1150 includes a third FC 1154 that includes a (third) MFC 1118, and a (third) inlet-side microfluidic device 1126. FIG. 11 also shows a portion of a first GC column 552A and a second GC column 552B. For simplicity, the third GC column of the third GC unit 1150 is not shown.

In the present embodiment, the first GC unit 500A and second GC unit 500B are positioned as upstream units that may receive separate sample injections, as shown in the diagram. The third GC unit 1150 positioned as a downstream unit, and is fluidly coupled to the first GC unit 500A and second GC unit 500B so as to be able to receive the respective effluents from the first GC column 552A and second GC column 552B. Hence, the GC device 1100 is configured for merging the sample streams from the first GC unit 500A and second GC unit 500B into a single sample stream in the third GC unit 1150, which may then flow to a detector as shown in the diagram.

As one example of such a configuration, the GC columns are fluidly coupled to the inlet-side and outlet side first ports of the respective GC units 500A, 500B, and 1150 as described above (e.g., FIG. 2A). The first FPC 526A and second FPC 526B are fluidly coupled to the third ports of the respective first outlet-side microfluidic device 558A and second outlet-side microfluidic device 558B, thereby providing respective first and second auxiliary carrier gas flows $F_{AUX1}$ and $F_{AUX2}$. The carrier gas line between the second FPC 526B and the third port of the second outlet-side microfluidic device 558B may be or include a flow restrictor 1164, which ensures that flow in the downstream (third) GC column of the third GC unit 1150 is controlled solely by a single FPC, i.e., the first FPC 526A and not the second FPC 526B. The fourth port of the first outlet-side microfluidic device 558A is fluidly coupled to the third port of the third inlet-side microfluidic device 1126, and the fourth port of the second outlet-side microfluidic device 558B is fluidly coupled to the second port of the third inlet-side microfluidic device 1126. The second ports of the first outlet-side microfluidic device 558A and second outlet-side microfluidic device 558B may communicate with other fluidic components (not shown). The third FC output port of the third GC unit 1150 is configured as a single output port that conducts carrier gas flow regulated by the third MFC 1118 to the fourth port of the third inlet-side microfluidic device 1126 via a single carrier gas line 1134.

The GC device 1100 is configured for implementing additive merging. This may be done by setting the MFC-regulated carrier gas flow $F_{MFC}$ from the third GC unit 1150 to a small value, and setting the total flow $F_{COL}$ through the third GC column to be greater than the sum of the total flows $F_{COL1}$ and $F_{COL2}$ into the first GC column 552A and second GC column 552B, i.e., $F_{COL} > F_{COL1} + F_{COL2}$. The GC device 1100 is also configured for implementing selective merging with backflushing. This may be done by lowering the GC column inlet pressure of the GC unit in need of backflushing.

Figure 12:
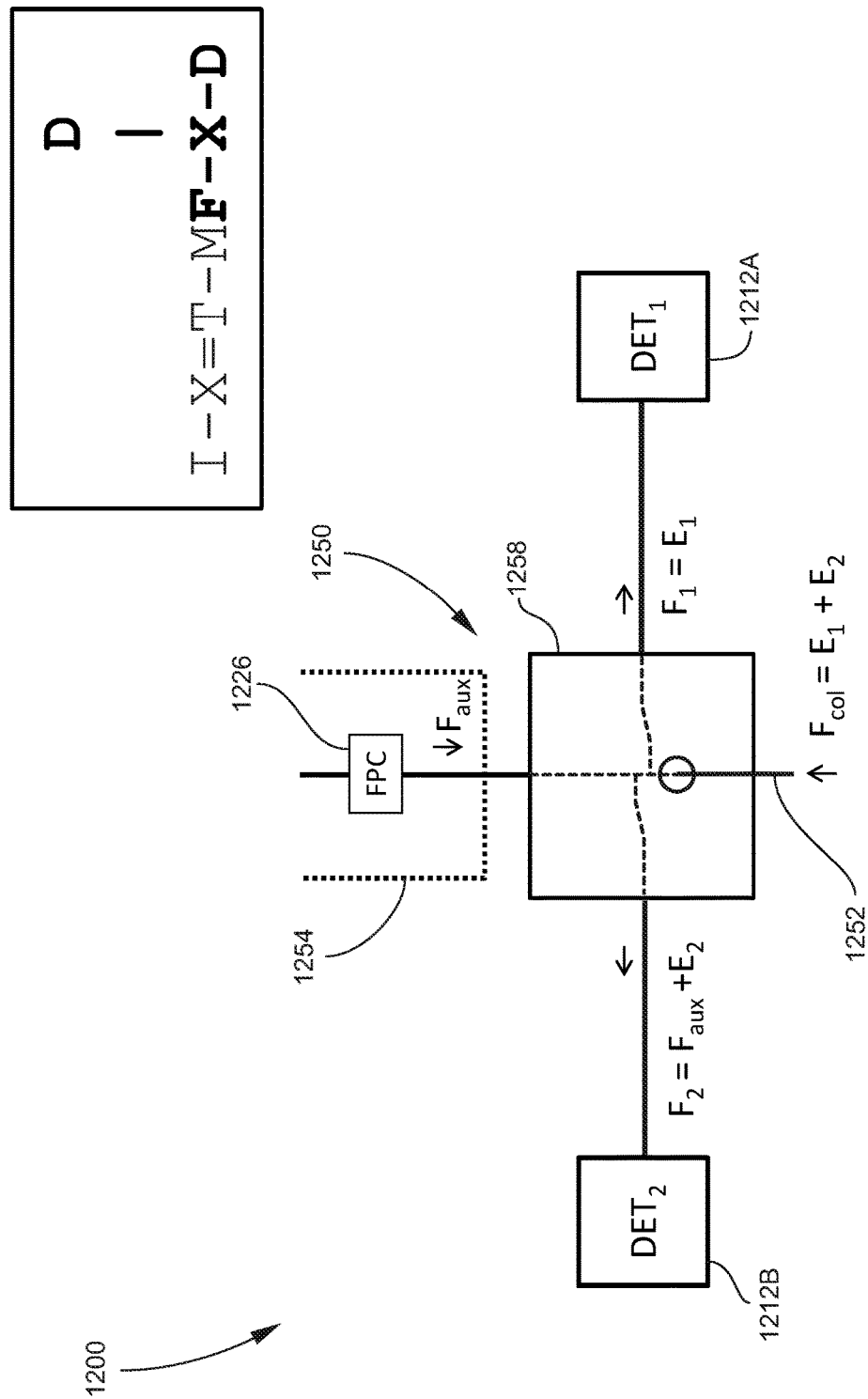
FIG. 12 is a schematic view of an example of a GC device (or a portion thereof) according to another embodiment.

FIG. 12 is a schematic view of an example of a GC device 1200 (or a portion thereof) according to another embodiment. The GC device 800 includes at least one upstream GC unit 1250, a first downstream detector 1212A, and a second downstream detector 1212B. For simplicity, FIG. 12 illustrates only the outlet side of the GC unit 1250. However, FIG. 12 also includes a diagram of an example of a more complete GC device 1200 and associated GC system using the notation presented in the TABLE above. As shown or partially shown in FIG. 12, the GC unit 1250 includes an FC 1254 that includes an FPC 1226, and an outlet-side microfluidic device 1258. FIG. 12 also shows a portion of a GC column 1252 fluidly coupled to the first port of the second GC unit 850.

In the present embodiment, the GC unit 1250 is positioned as an upstream unit that receives sample injections, as shown in the diagram. The first detector 1212A and second detector 1212B are positioned as downstream units, and are fluidly coupled to the GC unit 1250 so as to be able to receive the effluent from the GC column 1252. The GC device 1200 may be configured for implementing at least two modes of operation, fixed-ratio effluent splitting and tunable effluent splitting.

Generally, the GC device 1200 may be configured for implementing fixed-ratio effluent splitting by fluidly coupling the FPC 1226 (i.e., the carrier gas line regulated by the FPC 1226), the first detector 1212A, and the second detector 1212B arbitrarily to the second, third, and fourth ports of the outlet-side microfluidic device 1258. FIG. 12 illustrates one non-limiting example in which the FPC 1226 is fluidly coupled to the third port, the first detector 1212A is fluidly coupled to the second port, and the second detector 1212B is fluidly coupled to the fourth port. The setting on the FPC 1226 ($F_{AUX}$) determines the total flow $F_1$ and $F_2$ into the detectors 1212A and 1212B, i.e., $F_{AUX}=F_1+F_2-F_{COL}$. The flow ratio $F_1:F_2$ is fixed by the flow resistance ratio of the fluidic connections to the detectors 1212A and 1212B. Hence, by keeping $F_{AUX}$ constant, the effluent split ratio $E_1:E_2$ is likewise fixed.

Generally, the GC device 1200 may be configured for implementing tunable effluent splitting by fluidly coupling the FPC 1226 to the port that is not the one nearest to the port coupled to the GC column 1252 (i.e., not the second portion), and fluidly coupling the first detector 1212A and the second detector 1212B to the other two available ports of the outlet-side microfluidic device 1258. FIG. 12 illustrates one non-limiting example in which the FPC 1226 is fluidly coupled to the third port, the first detector 1212A is fluidly coupled to the second port, and the second detector 1212B is fluidly coupled to the fourth port. The effluent split ratio $E_1:E_2$ is tuned (varied) by changing the setting on the FPC 1226 ($F_{AUX}$). Because the flow ratio $F_1:F_2$ remains fixed, the effluent split ratio $E_1:E_2$ must change in response to changing $F_{AUX}$.

Figure 13:
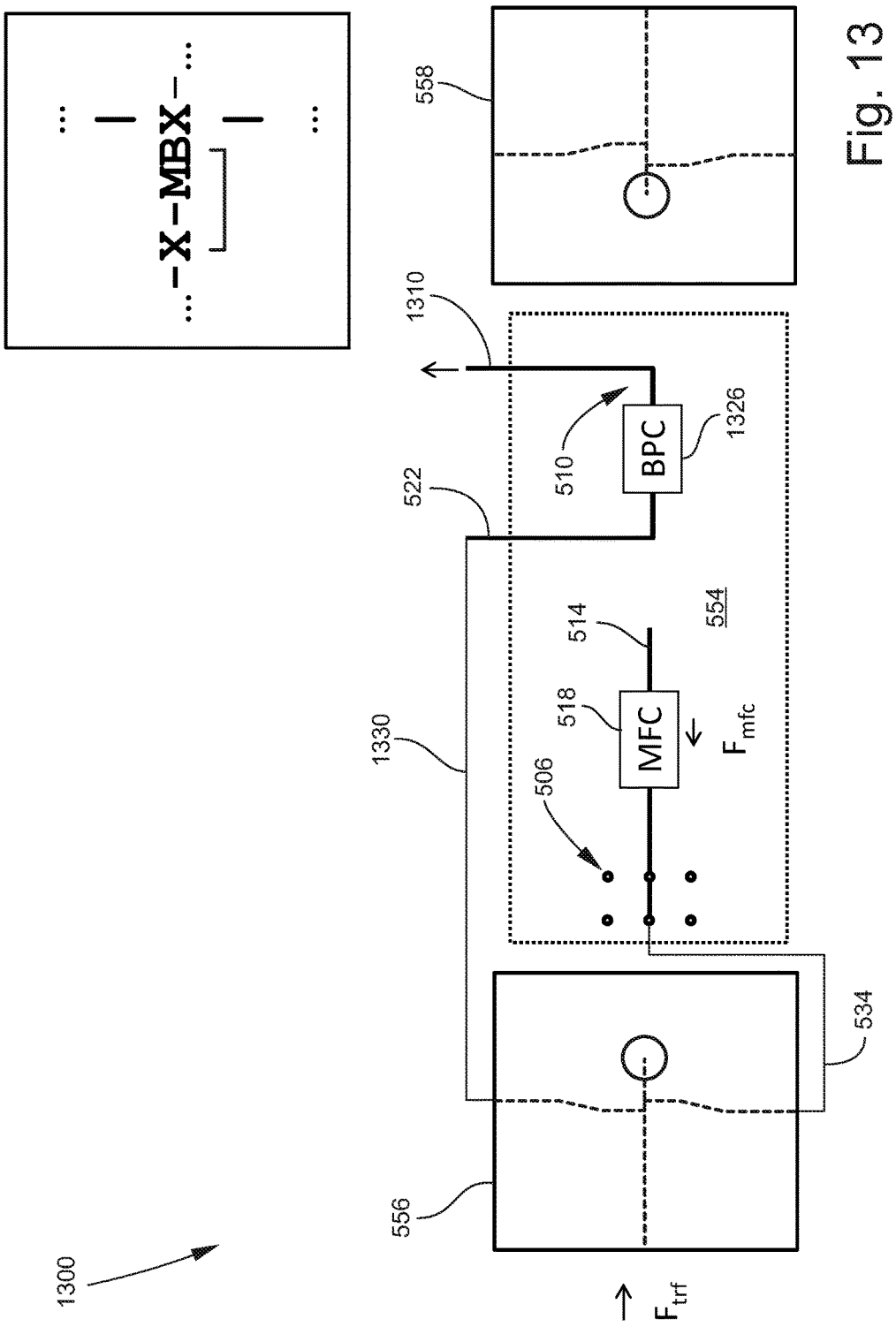
FIG. 13 is a schematic view of an example of a GC unit (or a GC device including the GC unit) according to another embodiment.

FIG. 13 is a schematic view of an example of a GC unit 1300 (or a GC device including the GC unit 1300) according to another embodiment. FIG. 13 also includes a diagram of the GC unit 1300 using the notation presented in the TABLE above. The GC unit 1300 may generally include the same components as, or components similar to, the components of the GC unit 500 described above in conjunction with FIG. 5. However, the GC unit 1300 is configured differently than the GC unit 500, or in some embodiments may be a reconfigured version of the GC unit 500. Specifically, the first FC output port 506 is configured as a single output port that conducts the carrier gas flow $F_{MFC}$ regulated by the MFC 518 to the fourth port 574 of the inlet-side microfluidic device 556 via the carrier gas line 534. The pressure controller of the FC 554 is configured as a BPC 1326 that communicates with the second port 570 of the inlet-side microfluidic device 556 via the carrier gas line 522 (and any additional gas line 1330 as needed to complete the fluidic connection). The second FC output port 510 communicating with the BPC-regulated carrier gas line 522 serves as, or communicates with, a vent 1310 for venting the BPC-regulated carrier gas flow $F_{VNT}$. A sample flow $F_{TRF}$ may be received at the third port of the inlet-side microfluidic device 556. The inlet and outlet ends of the GC column (not shown) may be fluidly coupled to the respective first ports of the inlet-side microfluidic device 556 and outlet-side microfluidic device 558. By this configuration, the column flow $F_{COL}$ is backpressure-controlled by the local BPC 1326, and $F_{COL}=F_{TRF}+F_{MFC}-F_{VNT}$.

Figure 14:
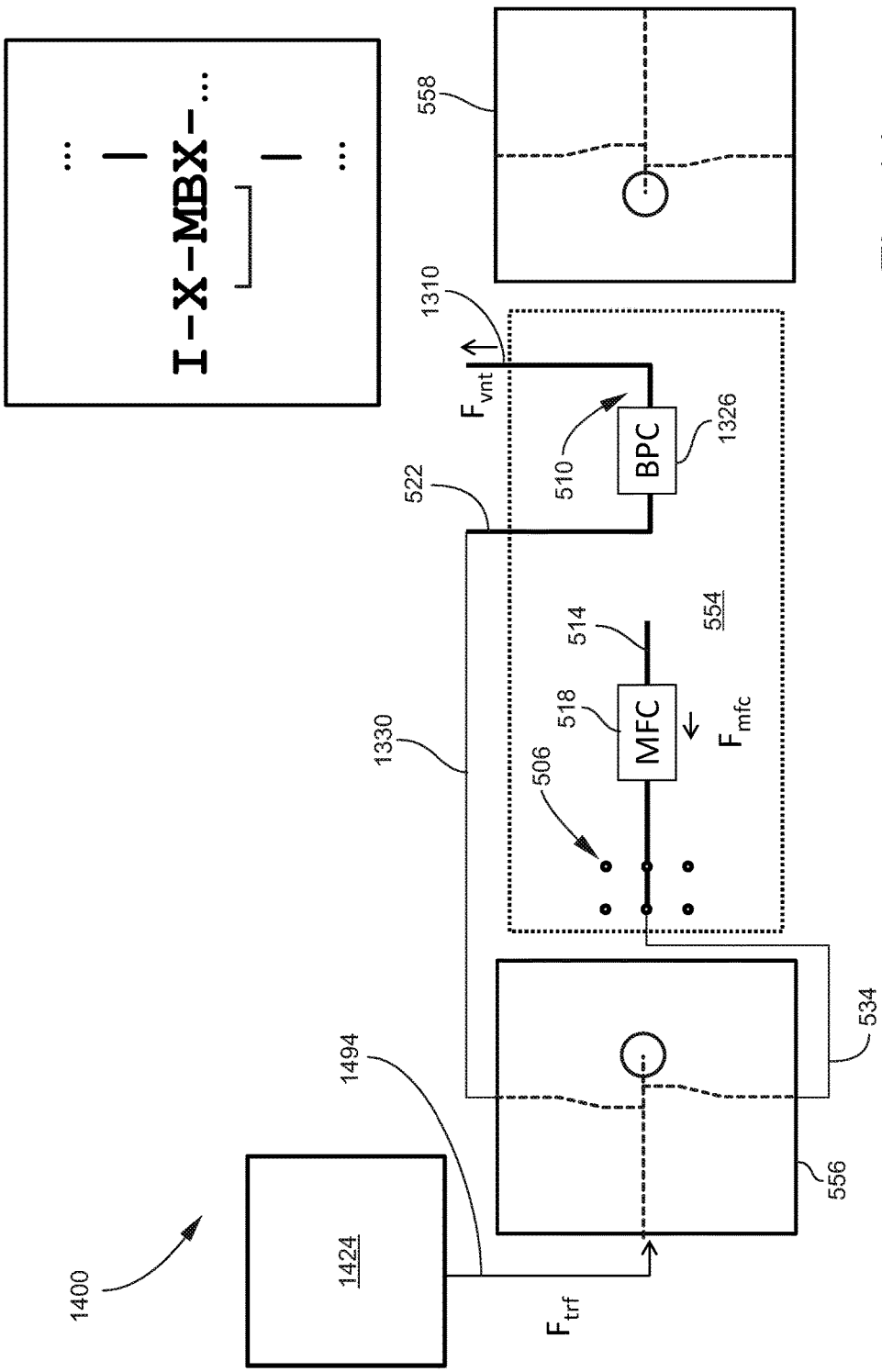
FIG. 14 is a schematic view of an example of a GC device (or a portion thereof) according to another embodiment.

FIG. 14 is a schematic view of an example of a GC device 1400 (or a portion thereof) according to another embodiment. The GC device 1400 includes the GC unit 1300 as described above, and a sample introduction device or gas sampler 1424 communicating with the third port of the inlet-side microfluidic device 556. The gas sampler 1424 may be a mass flow-controlled gas sampler such as, for example, a thermal desorber, a headspace sampler, or a gas sampling valve. The gas sampler 1424 may be coupled to the GC device 1400 through utilize a standard S/SL GC inlet. However, with the use of the backpressure-controlled GC unit 1300, a GC inlet may be eliminated and instead the gas sampler 1424 may be directly coupled to the inlet-side microfluidic device 556, which may be desirable in certain situations.

Figure 15:
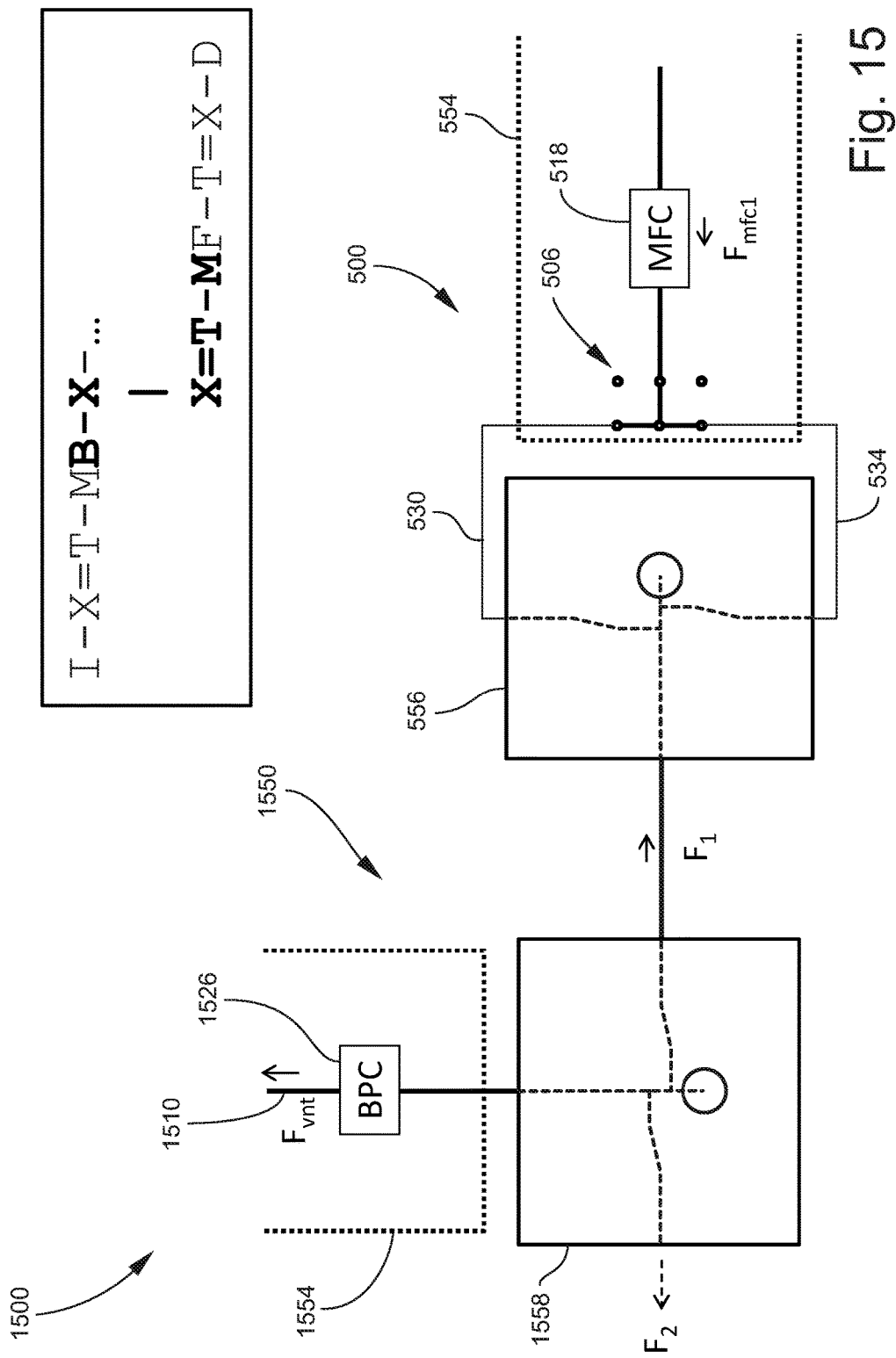
FIG. 15 is a schematic view of an example of a GC device (or a portion thereof) according to another embodiment.

FIG. 15 is a schematic view of an example of a GC device 1500 (or a portion thereof) according to another embodiment. The GC device 900 includes at least a first GC unit 500 and a second GC unit 1550. For simplicity, FIG. 15 illustrates only the inlet side of the first GC unit 500 and the outlet side of the second GC unit 1550. However, FIG. 15 also includes a diagram of an example of a more complete GC device 900 and associated GC system using the notation presented in the TABLE above. As shown or partially shown in FIG. 15, the first GC unit 500 includes a first FC 554 that includes an MFC 518, and a (first) inlet-side microfluidic device 556. The second GC unit 1550 includes a second FC 1554 that includes a pressure controller configured as a BPC 1526, and a (second) outlet-side microfluidic device 1558. The first GC unit 500 may generally be configured the same the GC unit 500 described above in conjunction with FIG. 5. The second GC unit 1550 is positioned as an upstream unit that receives sample injections, as shown in the diagram. The first GC unit 500 is positioned as a downstream unit that may be fluidly coupled to a detector as shown in the diagram. The GC column (not shown) of the first GC unit 500 is thus able to receive the effluent from the GC column (not shown) of the second GC unit 1550.

As one example of a configuration of the present embodiment, the gas line regulated by the BPC 1526 of the second GC unit 1550 communicates with the third port of the second outlet-side microfluidic device 1558 and conducts excess gas flow to a vent 1510. The fourth port of the second outlet-side microfluidic device 1558 is fluidly coupled to the third port of the first inlet-side microfluidic device 556. An additional downstream fluidic component (e.g., a GC unit or detector, not shown) may be coupled to the second port of the second outlet-side microfluidic device 1558, such that the effluent from the GC column of the upstream (second) GC unit 1550 may be split into a flow $F_1$ into the downstream (first) GC unit 500 and a flow $F_2$ into the additional downstream fluidic component. This configuration may be useful when column flow in the upstream GC unit 1550 is greater than the sum of the optimal column flows in the first GC unit 500 and the additional downstream fluidic component. In this case, the upstream GC unit 1550 enables excess flow to be vented through the BPC-regulated vent 1510. The GC device 1500 may be utilized for selective cutting of the effluent flow from the upstream GC unit 1550. To receive sample flow into the GC column of the first GC unit 500, the MFC-regulated flow $F_{MFC1}$ is set to be less than the column flow through the first GC unit 500 ($F_{MFC1}<F_{COL1}$). To reject the sample flow into the GC column of the first GC unit 500, the MFC-regulated flow $F_{MFC1}$ is set to be greater than the column flow through the first GC unit 500 ($F_{MFC1} > F_{COL1}$).

Figure 16:
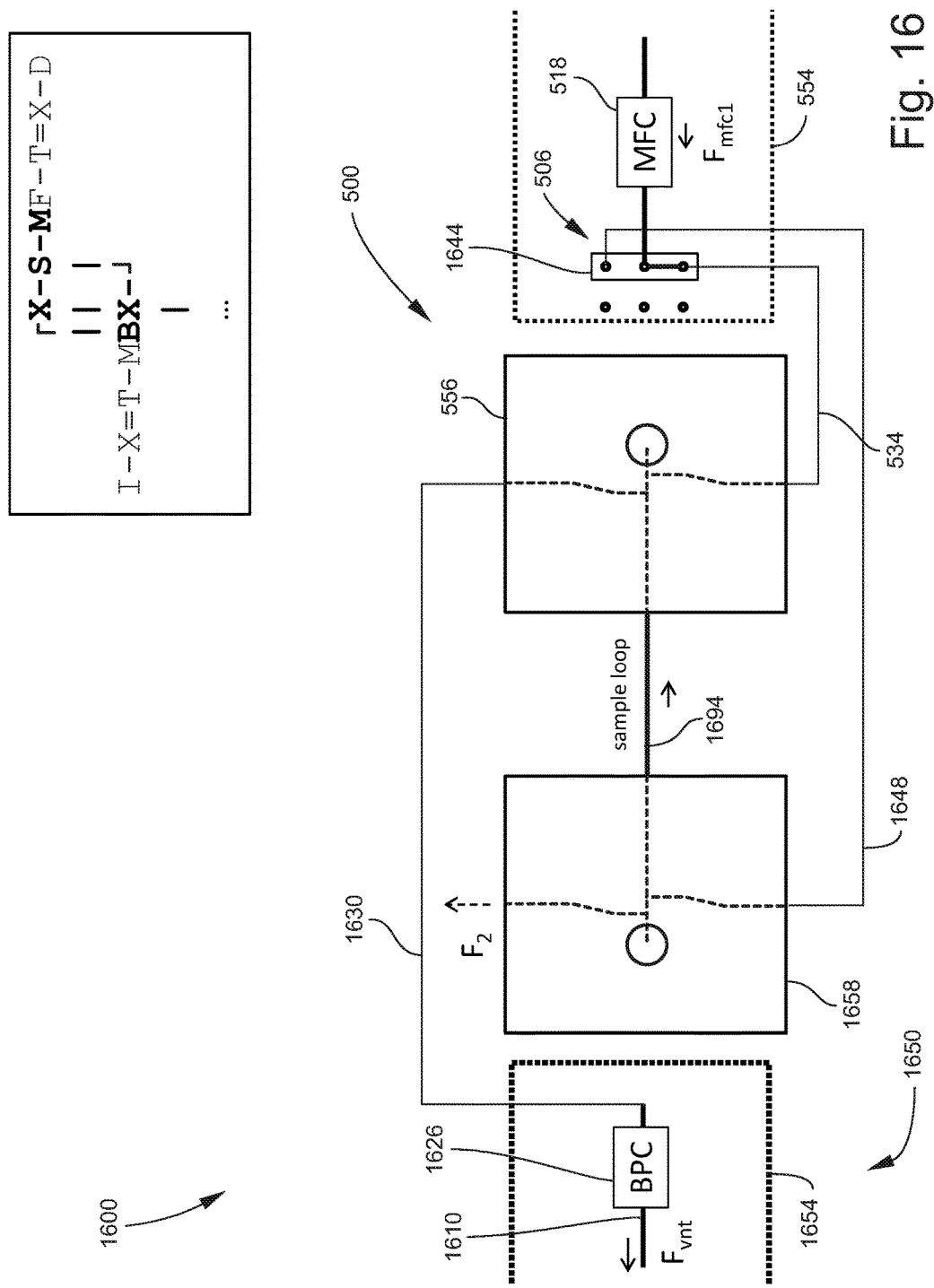
FIG. 16 is a schematic view of an example of a GC device (or a portion thereof) according to another embodiment.

FIG. 16 is a schematic view of an example of a GC device 1600 (or a portion thereof) according to another embodiment. The GC device 1600 includes at least a first GC unit 500 and a second GC unit 1650. For simplicity, FIG. 16 illustrates only the inlet side of the first GC unit 500 and only the outlet side of the second GC unit 1650. However, FIG. 16 also includes a diagram of an example of a more complete GC device 1600 and associated GC system using the notation presented in the TABLE above. As shown or partially shown in FIG. 16, the first GC unit 500 includes a first FC 554 that includes a first MFC 518, and a first inlet-side microfluidic device 556; and the second GC unit 1650 includes a second FC 1654 that includes a (second) BPC 1626, and a (second) outlet-side microfluidic device 1658.

In the present embodiment, the second GC unit 1650 is positioned as an upstream unit that receives sample injections, as shown in the diagram. The first GC unit 500 is positioned as a downstream unit, and is fluidly coupled to the second GC unit 1650 so as to be able to receive the effluent from the GC column of the second GC unit 1650. As shown in the diagram, the first GC unit 500 may communicate with a detector. In some embodiments, an additional downstream fluidic component (e.g., a GC unit or detector, not shown) may also be fluidly coupled to the fourth port ($F_2$) the second GC unit 1650 (the second outlet-side microfluidic device 1658) so as to be able to receive the effluent from the GC column of the second GC unit 1650. Otherwise, the first GC unit 500 may be fluidly coupled to the fourth port the second GC unit 1650 (not shown).

The GC device 1600 is configured for implementing GC×GC flow modulation with flow splitting occurring before the second dimension (i.e., before the GC column of the first GC unit 500). As one non-limiting example of configuring the GC device 1600 for implementing this mode, the GC columns are fluidly coupled to the inlet-side and outlet side first ports of the respective GC units 500 and 1650. The first MFC 518 is fluidly coupled to the fourth port of the first inlet-side microfluidic device 556 via a carrier gas line 534, but in the present embodiment this coupling is selectable as described below. The second outlet-side microfluidic device 1658 is positioned such that the second BPC 1626 communicates with the second port of the first inlet-side microfluidic device 556 via a carrier gas line 1630. The second outlet-side microfluidic device 1658 is oriented such that its third port communicates with the third port of the first inlet-side microfluidic device 556 via a sample loop 1694.

Also in the present embodiment, the first FC output port 506 has been configured to include a switch valve 1644 between the first MFC 518 and two selectable output ports of the first FC output port 506. The switch valve 1644 is movable between a first position and a second position. At the first position, illustrated in FIG. 16, the switch valve 1644 directs carrier gas from the first MFC 518 to the first inlet-side microfluidic device 556A via the gas line 534 as described above. At the second position, the switch valve 1644 directs the carrier gas from the first MFC 518 to the second port of the second outlet-side microfluidic device 1658 via another carrier gas line 1648. Thus, the first position may be utilized for filling the sample loop 1694, and the second position may be utilized for flushing the sample loop 1694.

Figure 17:
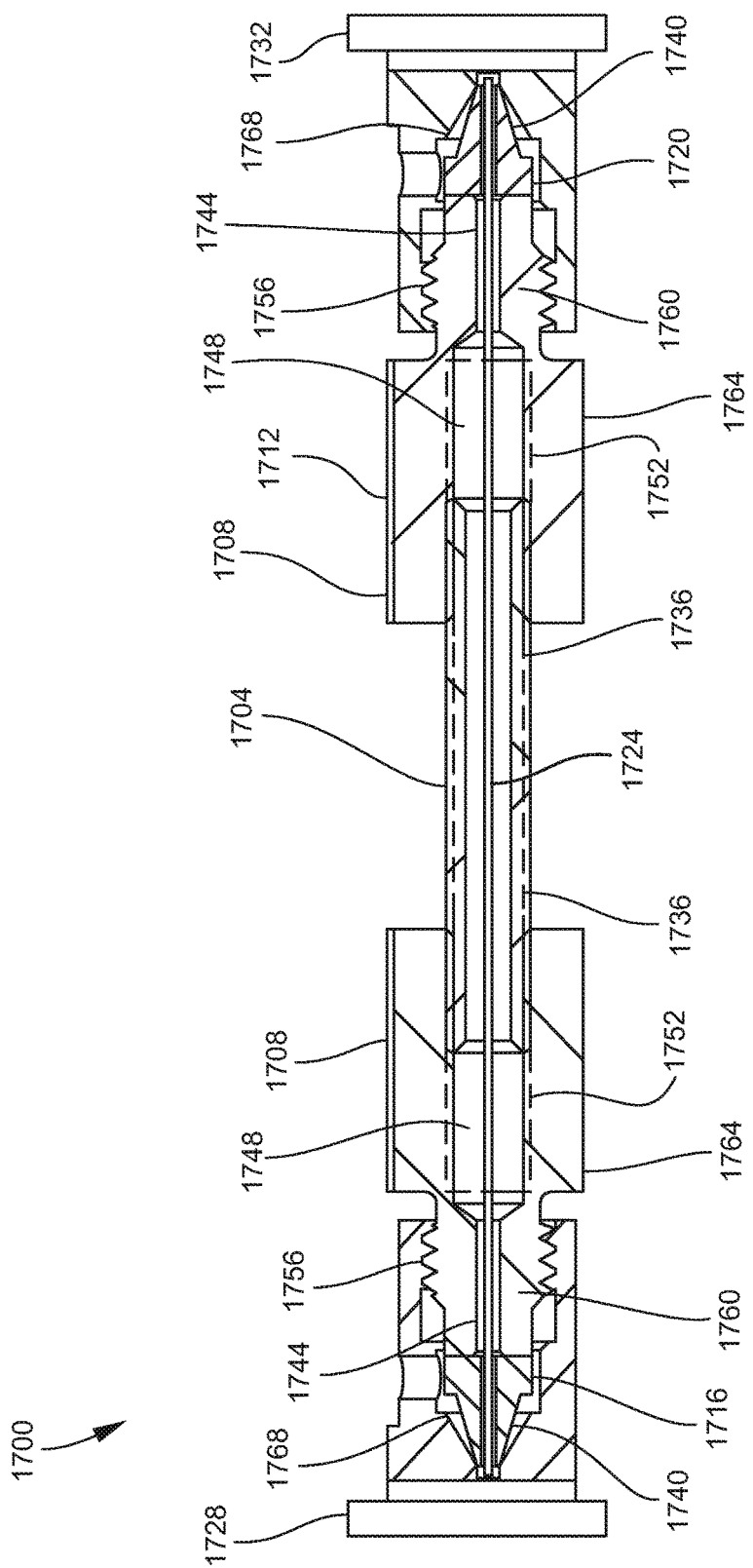
FIG. 17 is a schematic cross-sectional view of a transfer line assembly according to some embodiments.

FIG. 17 is a schematic cross-sectional view of a transfer line assembly 1700 according to some embodiments. The transfer line assembly 1700 allows two fluidic devices, such as two microfluidic device of two respective GC units as described herein, to be fluidly coupled together in a gas-tight manner by a transfer line (or conduit) 1704. Moreover, the transfer line assembly 1700 enables the transfer line 1704 to be passively heated, such as by heaters provided by the two GC units, so as to avoid cold spots or zones between the GC units. In the illustrated embodiment, the transfer line assembly 1700 includes the transfer line 1704, a first retaining nut 1708, a second retaining nut 1712, a first sealing member 1716, a second sealing member 1720, and a capillary (conduit) 1724. The retaining nuts 1708 and 1712 are configured for being fluidly coupled to respective fittings of the microfluidic devices. FIG. 17 illustrates a first fitting 1728 and a second fitting 1732. Respective ports of the microfluidic devices may be, or include, or fluidly communicate with the first fitting 1728 and the second fitting 1732.

The transfer line 1704 includes respective outer threads 1736 at its opposing ends, or a continuous outer thread 1736 may extend along the entire length of the transfer line 1704 or a substantial length thereof. Each sealing member 1716 and 1720 may include an inner bore through which the capillary 1724 passes, and an outer tapered (or conical) portion 1740. Thus, in the illustrated embodiment the sealing members 1716 and 1720 are ferrules as appreciated by persons skilled in the art.

Each retaining nut 1708 and 1712 includes an inner bore through which the capillary 1724 passes. The inner bore may include a first bore 1744 large enough to accommodate the capillary 1724, and a second bore 1748 large enough to receive an end of the transfer line 1704. The second bore 1748 thus may have a larger diameter than the first bore 1744. The second bore 1748 includes an inner thread 1752 configured for mating engagement with the outer thread 1736 of the transfer line 1704. Each retaining nut 1708 and 1712 also includes an outer thread 1756. Each retaining nut 1708 and 1712 may include a first (or front) section 1760 at which the first bore 1744 and outer thread 1756 are located, and a second (or back) section 1764 at which the second bore 1748 and inner thread 1752 are located. The axial length of the second section 1764 may be greater than the axial length of the first section 1760. In some embodiments, the axial length of the second section 1764 is at least twice the axial length of the first section 1760. The relatively greater length of the second section 1764 may be desirable for two reasons. First, the increased length accommodates a longer capillary 1724, thereby providing the ability to make a few cut-backs (i.e., trimming) of the capillary 1724 in conjunction with one or more reinstallations. Second, the increased length increases the forward/backward distance over which the retaining nut 1708 or 1712 may be moved (by turning, or threading) along the transfer line 1704, which may facilitate installation and removal of the retaining nut 1708 or 1712.

Each fitting 1728 and 1732 includes an inner bore sized to receive at least the portion of the retaining nut 1708 and 1712 that includes the outer thread 1756. The inner bore of the fitting 1728 and 1732 includes an inner thread configured for mating engagement with the outer thread 1756 of the retaining nut 1708 and 1712. The inner bore of the fitting 1728 and 1732 may also include an inner tapered (or conical) portion 1768 configured to receive the outer tapered (or conical) portion 1740 of the sealing member 1716 and 1720. The outer tapered portion 1740 of the sealing members 1716 and 1720 may be tapered at a different angle than the inner tapered portion 1768 of the fittings 1728 and 1732.

A non-limiting example of assembling the transfer line assembly 1700 will now be described. Persons skilled in the art will appreciate that the order of assembly steps described herein may be modified, and that one or more steps may be varied from the present example. The transfer line 1704 is threaded into the first retaining nut 1708. The capillary 1724 is inserted through the first sealing member 1716, the first retaining nut 1708, and the capillary 1724. The first sealing member 1716 is then inserted into the inner bore of the first fitting 1728. The first retaining nut 1708 is then threaded into the first fitting 1728, forcing the outer tapered portion 1740 of the first sealing member 1716 to bear against the inner tapered portion 1768 of the first fitting 1728. Thus, the first sealing member 1716 is in bearing contact (or forced contact) with the first fitting 1728 and the first retaining nut 1708, and in some embodiments may be characterized as being compressed between the first fitting 1728 and the first retaining nut 1708. As appreciated by persons skilled in the art, the bearing contact between the outer tapered portion 1740 and inner tapered portion 1768 imparts force(s) having both axial and radial components and results in a gas-tight seal between (or at the interface of) the first sealing member 1716 and the first fitting 1728. The first sealing member 1716 is also in bearing contact with the capillary 1724, thereby forming a gas-tight seal in the inner bore of the first sealing member 1716. The second retaining nut 1712 may then be threaded onto the transfer line 1704, and threaded into the second fitting 1732 in an analogous manner to produce a gas-tight seal between the second sealing member 1720 and the second fitting 1732 and between the second sealing member 1720 and the capillary 1724. Upon completion of the assembly process, the microfluidic devices associated with the first fitting 1728 and the second fitting 1732 are fluidly coupled, with the capillary 1724 communicating with internal channels of the microfluidic devices.

Exemplary Embodiments

Exemplary embodiments provided in accordance with the presently disclosed subject matter include, but are not limited to, the following:

1. A gas chromatographic (GC) unit, comprising: an inlet-side microfluidic device comprising a plurality of inlet-side channels and a plurality of inlet-side ports, each inlet-side port communicating with at least one of the inlet-side channels; an outlet-side microfluidic device comprising a plurality of outlet-side channels and a plurality of outlet-side ports, each outlet-side port communicating with at least one of the outlet-side channels; a column comprising a column inlet coupled to a first inlet-side port of the plurality of inlet-side ports, and a column outlet coupled to a first outlet-side port of the plurality of outlet-side ports; and a flow controller (FC) comprising an FC input port for receiving a flow of carrier gas, a first FC output port communicating with the FC input port, and a second FC output port communicating with the FC input port, wherein the first FC output port communicates with an additional inlet-side port of the plurality of inlet-side ports.

2. The GC unit of embodiment 1, wherein the second FC output port communicates with an additional outlet-side port of the plurality of outlet-side ports.

3. The GC unit of embodiment 2, wherein the FC comprises a configuration selected from the group consisting of: the first FC output port communicates with at least two of the inlet-side ports; the second FC output port communicates with at least two of the outlet-side ports; and both of the foregoing.

4. The GC unit of embodiment 2, wherein the FC comprises a forward pressure controller configured for controlling a flow of carrier gas to the second FC output port.

5. The GC unit of embodiment 2, wherein the FC input port comprises a first carrier gas line communicating with the first FC output port, a mass flow controller configured for controlling a first carrier gas flow from the FC input port to the first FC output port, a second carrier gas line communicating with the second FC output port, and a forward pressure controller configured for controlling a second carrier gas flow from the FC input port to the second FC output port.

6. The GC unit of embodiment 5, wherein: the plurality of inlet-side ports comprises the first inlet-side port, a second inlet-side port, a third inlet-side port, and a fourth inlet-side port; the plurality of outlet-side ports comprises the first outlet-side port, a second outlet-side port, a third outlet-side port, and a fourth outlet-side port; the first FC output port is configured for directing a portion of the first carrier gas flow to the second inlet-side port and another portion of the first carrier gas flow to the fourth inlet-side port; and the second FC output port is configured for directing a portion of the second carrier gas flow to the second outlet-side port and another portion of the second carrier gas flow to the fourth outlet-side port.

7. A gas chromatographic (GC) device, comprising: the GC unit of embodiment 1; and a fluidic device selected from the group consisting of: a sample introduction device communicating with at least one of the inlet-side ports; a detector communicating with at least one of the outlet-side ports; an additional GC unit communicating with at least one of the inlet-side ports or outlet-side ports; and two or more of the foregoing.

8. The GC device of embodiment 7, wherein: the plurality of inlet-side ports comprises the first inlet-side port, a second inlet-side port, a third inlet-side port, and a fourth inlet-side port; the first FC output port communicates with one or both of the second inlet-side port and the fourth inlet-side port; and the sample introduction device communicates with the third inlet-side port.

9. The GC device of embodiment 7, wherein: the plurality of outlet-side ports comprises the first outlet-side port, a second outlet-side port, a third outlet-side port, and a fourth outlet-side port; the second FC output port communicates with one or both of the second outlet-side port and the fourth outlet-side port; and the detector communicates with the third outlet-side port.

10. The GC device of embodiment 7, wherein the GC unit is a first GC unit, the inlet-side microfluidic device is a first inlet-side microfluidic device, the outlet-side microfluidic device is a first outlet-side microfluidic device, the column is a first column, and the FC is a first FC, and further comprising: a second GC unit comprising a second inlet-side microfluidic device, a second outlet-side microfluidic device, a second column communicating with the second inlet-side microfluidic device and the second outlet-side microfluidic device, and a second FC communicating with the second inlet-side microfluidic device and the second outlet-side microfluidic device, wherein the second inlet-side microfluidic device communicates with the first outlet-side microfluidic device, and the detector communicates with the second outlet-side microfluidic device.

11. A gas chromatographic (GC) device, comprising: a first GC unit according to embodiment 1; a second GC unit according to embodiment 1; and a third GC unit according to embodiment 1, wherein the inlet-side microfluidic devices of the first GC unit and the second GC unit communicate with respective ports of the outlet-side microfluidic device of the third GC unit.

12. The GC device of embodiment 11, comprising at least one of: a sample introduction device communicating with the inlet-side microfluidic device of the third GC unit; a detector communicating with the outlet-side microfluidic device of the first GC unit; and a detector communicating with the outlet-side microfluidic device of the second GC unit.

13. A gas chromatographic (GC) device, comprising: a first GC unit according to embodiment 1; a second GC unit according to embodiment 1; and a detector, wherein the inlet-side microfluidic device of the first GC unit and the detector communicate with respective ports of the outlet-side microfluidic device of the second GC unit.

14. The GC device of embodiment 13, wherein: the first FC output port of the first GC unit comprises a switch movable between a first position and a second position; at the first position, the switch conducts carrier gas from the FC of the first GC unit to the inlet-side microfluidic device of the first GC unit; and at the second position, the switch conducts at least a portion of the carrier gas from the FC of the first GC unit to the second GC unit such that the portion bypasses the inlet-side microfluidic device of the first GC unit.

15. The GC device of embodiment 13 or 14, comprising at least one of: a sample introduction device communicating with the inlet-side microfluidic device of the second GC unit; and a detector communicating with the outlet-side microfluidic device of the first GC unit.

16. A gas chromatographic (GC) device, comprising: a first GC unit according to embodiment 1; a second GC according to embodiment 1, wherein: the outlet-side microfluidic device of the second GC unit communicates with the inlet-side microfluidic device of the first GC unit via a sample loop; the FC output port of the first GC unit comprises a switch movable between a first position and a second position; at the first position, the switch conducts carrier gas from the FC of the first GC unit to the inlet-side microfluidic device of the first GC unit; and at the second position, the switch conducts carrier gas from the FC of the first GC unit to the second GC unit such that the carrier gas bypasses the inlet-side microfluidic device of the first GC unit.

17. The GC device of embodiment 16, comprising at least one of: a sample introduction device communicating with the inlet-side microfluidic device of the second GC unit; a fluidic device communicating with the outlet-side microfluidic device of the second GC unit; and a detector communicating with the outlet-side microfluidic device of the first GC unit.

18. A gas chromatographic (GC) device, comprising: a first GC unit according to embodiment 1; a second GC unit according to embodiment 1; and a third GC unit according to embodiment 1, wherein the outlet-side microfluidic devices of the first GC unit and the second GC unit communicate with respective ports of the inlet-side microfluidic device of the third GC unit.

19. The GC device of embodiment 18, comprising at least one of: a sample introduction device communicating with the inlet-side microfluidic device of the first GC unit; a sample introduction device communicating with the inlet-side microfluidic device of the second GC unit; a fluidic device communicating with the outlet-side microfluidic device of the first GC unit; a fluidic device communicating with the outlet-side microfluidic device of the second GC unit; and a detector communicating with the outlet-side microfluidic device of the third GC unit.

20. A gas chromatographic (GC) device, comprising: the GC unit of embodiment 1; and a first detector and a second detector communicating with respective ports of the outlet-side microfluidic device.

21. The GC unit of embodiment 20, wherein: the plurality of outlet-side ports comprises, in addition to the first outlet-side port, a second port, a third port, and a fourth port; the plurality of outlet-side channels comprises a first channel communicating with the first outlet-side port, a second channel communicating with the second port, a third channel communicating with the third port, and a fourth channel communicating with the fourth port; respective inside ends of the first channel, the second channel, the third channel, and the fourth channel are positioned such that the inside end of the second channel is between the inside end of the first channel and the inside end of the third channel, the inside end of the second channel is also between the inside end of the third channel and the inside end of the fourth channel, the inside end of the fourth channel is between the inside end of the first channel and the inside end of the second channel, and the inside end of the fourth channel is also between the inside end of the first channel and the inside end of the third channel; the second FC output port communicates with the third port; the first detector communicates with the fourth port; and the second detector communicates with the second port.

22. The GC unit of embodiment 20, comprising a sample introduction device communicating with the inlet-side microfluidic device.

23. The GC unit of embodiment 1, wherein the FC input port comprises a first FC input port and a second FC input port, the first FC input port communicates with the first FC input port, the second FC input port communicates with the second FC output port, and the second FC output port is configured for venting gas from the GC unit.

24. The GC unit of embodiment 23, wherein the second FC input port communicates with the inlet-side microfluidic device or the outlet-side microfluidic device.

25. The GC unit of embodiment 23, wherein: the plurality of inlet-side ports comprises, in addition to the first inlet-side port, a second port, a third port, and a fourth port; the plurality of inlet-side channels comprises a first channel communicating with the first inlet-side port, a second channel communicating with the second port, a third channel communicating with the third port, and a fourth channel communicating with the fourth port; respective inside ends of the first channel, the second channel, the third channel, and the fourth channel are positioned such that the inside end of the second channel is between the inside end of the first channel and the inside end of the third channel, the inside end of the second channel is also between the inside end of the third channel and the inside end of the fourth channel, the inside end of the fourth channel is between the inside end of the first channel and the inside end of the second channel, and the inside end of the fourth channel is also between the inside end of the first channel and the inside end of the third channel; the first FC output port communicates with the fourth port; and the second FC input port communicates with the second port.

26. The GC unit of embodiment 23, wherein the FC comprises a controller selected from the group consisting of: a mass flow controller configured for controlling a flow of carrier gas to the first FC output port; a back pressure controller configured for controlling a flow of gas from the second FC input port to the second FC output port; both of the foregoing.

27. A gas chromatographic (GC) device, comprising: the GC unit of embodiment 23; and a fluidic device selected from the group consisting of: a fluidic device communicating with at least one of the inlet-side ports; a sample introduction device communicating with at least one of the inlet-side ports; a fluidic device communicating with at least one of the outlet-side ports; a detector communicating with at least one of the outlet-side ports; and two or more of the foregoing.

28. A gas chromatographic (GC) device, comprising: a first GC unit according to embodiment 1; and a second GC unit according to embodiment 23, wherein respective ports of the outlet-side microfluidic device of the second GC unit communicate with the FC of the second GC unit and with the inlet-side microfluidic device of the first GC unit.

29. The GC device of embodiment 28, wherein the FC of the first GC unit comprises a mass flow controller configured for controlling a flow of carrier gas to the inlet-side microfluidic device of the first GC unit, and the FC of the second GC unit comprises a back pressure controller configured for controlling a flow of gas from the outlet-side microfluidic device of the second GC unit to the FC of the second GC unit.

30. The GC device of embodiment 28, comprising a fluidic device selected from the group consisting of: a sample introduction device communicating with the inlet-side microfluidic device of the second GC unit; a fluidic device communicating with the outlet-side microfluidic device of the second GC unit; a detector communicating with the outlet-side microfluidic device of the first GC unit; and two or more of the foregoing.

31. A gas chromatographic (GC) device, comprising: a first GC unit according to embodiment 1; and a second GC unit according to embodiment 23, wherein: the outlet-side microfluidic device of the second GC unit communicates with the inlet-side microfluidic device of the first GC unit via a sample loop; the first FC output port of the first GC unit comprises a switch movable between a first position and a second position; at the first position, the switch conducts carrier gas from the FC of the first GC unit to the inlet-side microfluidic device of the first GC unit; and at the second position, the switch conducts carrier gas from the FC of the first GC unit to the outlet-side microfluidic device of the second GC unit.

32. The GC device of embodiment 31, wherein the inlet-side microfluidic device of the first GC unit communicates with the second FC inlet of the second GC unit.

33. The GC device of embodiment 31, comprising a fluidic device selected from the group consisting of: a sample introduction device communicating with the inlet-side microfluidic device of the second GC unit; a detector communicating with the outlet-side microfluidic device of the first GC unit; and both of the foregoing.

34. The GC device of embodiment 31, wherein the plurality of outlet-side ports of the second GC unit comprises, in addition to the first outlet-side port, a second port communicating with the switch, and a third port communicating with the inlet-side microfluidic device of the first GC unit.

35. The GC device of embodiment 34, wherein the plurality of outlet-side ports of the second GC unit comprises a fourth port communicating with a fluidic device.

36. A gas chromatographic (GC) device, comprising: the GC unit of embodiment 1 or embodiment 23; and a fluidic device selected from the group consisting of: a fluidic device communicating with at least one of the inlet-side ports; a sample introduction device communicating with at least one of the inlet-side ports; an additional microfluidic device communicating with at least one of the inlet-side ports; a fluidic device communicating with at least one of the outlet-side ports; a detector communicating with at least one of the outlet-side ports; an additional microfluidic device communicating with at least one of the outlet-side ports; and two or more of the foregoing.

37. The GC unit of any of the preceding embodiments, wherein the inlet-side microfluidic device and the outlet-side microfluidic device comprise respective bodies, and the inlet-side channels and the outlet-side channels are formed in the respective bodies.

38. The GC unit of any of the preceding embodiments, wherein the inlet-side microfluidic device and the outlet-side microfluidic device each comprise a body, and a heater disposed at a location in or on the body suitable for heating fluid in the inlet-side channels or the outlet-side channels.

39. The GC unit of any of the preceding embodiments, wherein each inlet-side channel and each outlet-side channel has a characteristic dimension no greater than 1 mm.

40. The GC unit of any of the preceding embodiments, wherein for each of the inlet-side microfluidic device and the outlet-side microfluidic device, the plurality of inlet-side or outlet-side ports comprises, in addition to the first inlet-side or outlet-side port, a second port, a third port, and a fourth port, and the plurality of channels comprises a first channel communicating with the first port, a second channel communicating with the second port, a third channel communicating with the third port, and a fourth channel communicating with the fourth port.

41. The GC unit of embodiment 40, wherein respective inside ends of the first channel, the second channel, the third channel, and the fourth channel are positioned such that the inside end of the second channel is between the inside end of the first channel and the inside end of the third channel, the inside end of the second channel is also between the inside end of the third channel and the inside end of the fourth channel, the inside end of the fourth channel is between the inside end of the first channel and the inside end of the second channel, and the inside end of the fourth channel is also between the inside end of the first channel and the inside end of the third channel.

42. The GC unit of embodiment 40, wherein the inlet-side microfluidic device and the outlet-side microfluidic device each comprise a common channel communicating with respective internal ends of the first channel, the second channel, the third channel, and the fourth channel; and the common channel extends from a first junction at which the inside end of the second channel meets the inside end of the third channel, to a second junction at which the inside end of the first channel meets the inside end of the fourth channel; and wherein the inside end of the second channel is spaced from the inside end of the fourth channel by the common channel.

43. The GC unit of any of the preceding embodiments, wherein the FC comprises a mass flow controller configured for controlling a flow of carrier gas to the first FC output port.

44. The GC unit of any of the preceding embodiments, wherein at least one of the first FC output port and the second FC output port is reconfigurable to enable selection among a plurality of different flow paths through the first FC output port or the second FC output port.

45. The GC unit of any of the preceding embodiments, wherein the FC comprises an electronic pneumatic controller.

46. The GC unit of any of the preceding embodiments, comprising a transfer line threadedly engaged with at least one microfluidic device of the inlet-side microfluidic device and the outlet-side microfluidic device.

47. The GC unit of embodiment 46, wherein the at least one microfluidic device comprises a fitting and a retaining nut coupled to the fitting, wherein the transfer line is threadedly engaged with the retaining nut.

48. The GC unit of embodiment 47, comprising a sealing member in bearing contact with the fitting and the retaining nut.

49. The GC unit of embodiment 48, wherein the sealing member comprises a ferrule.

50. The GC unit of embodiment 47, wherein the retaining nut comprises a first section and a second section, the first section comprises a thread configured for engaging the fitting, the second section comprises a thread configured for engaging the transfer line, and the second section has an axial length greater than an axial length of the first section.

51. The GC unit of embodiment 50, wherein the axial length of the second section is at least twice the axial length of the first section.

52. The GC unit of any of embodiments 46 to 51, comprising a capillary in the transfer line and communicating with at least one channel of the at least one microfluidic device.

53. The GC unit of any of embodiments 46 to 52, wherein the at least one microfluidic device is a first microfluidic device, and further comprising a second microfluidic device threadedly engaged with the transfer line, wherein the transfer line is between the first microfluidic device and the second microfluidic device.

For purposes of the present disclosure, it will be understood that when a layer (or film, region, substrate, component, device, or the like) is referred to as being "on" or "over" another layer, that layer may be directly or actually on (or over) the other layer or, alternatively, intervening layers (e.g., buffer layers, transition layers, interlayers, sacrificial layers, etch-stop layers, masks, electrodes, interconnects, contacts, or the like) may also be present. A layer that is "directly on" another layer means that no intervening layer is present, unless otherwise indicated. It will also be understood that when a layer is referred to as being "on" (or "over") another layer, that layer may cover the entire surface of the other layer or only a portion of the other layer. It will be further understood that terms such as "formed on" or "disposed on" are not intended to introduce any limitations relating to particular methods of material transport, deposition, fabrication, surface treatment, or physical, chemical, or ionic bonding or interaction. The term "interposed" is interpreted in a similar manner.

As appreciated by persons skilled in the art, the computing device 116 schematically illustrated in FIG. 1 may include one or more reading devices on or in which a tangible computer-readable (machine-readable) medium may be loaded that includes instructions for performing all or part of any of the methods disclosed herein. The computing device 116 may include one or more types of hardware, firmware and/or software, as well as one or more memories and databases. The computing device 116 may include one or more types of user interface devices for input (e.g., keyboard, keypad, touch screen, mouse, joystick, trackball, and the like) and output (e.g., display screen, printer, visual indicators or alerts, audible indicators or alerts, and the like). The computing device 116 may also include one or more types of computer programs or software contained in memory and/or on one or more types of computer-readable media. Computer programs or software may contain instructions (e.g., logic instructions) for performing all or part of any of the methods disclosed herein. Computer programs or software may include application software and system software. System software may include an operating system (e.g., a Microsoft Windows® operating system) for controlling and managing various functions of the computing device, including interaction between hardware and application software. In particular, the operating system may provide a graphical user interface (GUI) displayable via a user output device such as a display screen, and with which a user may interact with the use of a user input device such as a keyboard or a pointing device (e.g., mouse). The computing device 116 may also include one or more data acquisition/signal conditioning components (as may be embodied in hardware, firmware and/or software) for receiving and processing ion measurement signals outputted by the detector(s) 112, including formatting data for presentation in graphical form by the GUI.

In general, terms such as "communicate" and "in . . . communication with" and "coupled" (for example, a first component "communicates with" or "is in communication with" a second component, or a first component "is coupled to" a second component) are used herein to indicate a structural, functional, mechanical, electrical, signal, optical, magnetic, electromagnetic, ionic or fluidic relationship between two or more components or elements. As such, the fact that one component is said to communicate with or be coupled to a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A gas chromatographic (GC) unit, comprising:
an inlet-side microfluidic device comprising an inlet body having a plurality of inlet-side channels and a plurality of inlet-side ports, each inlet-side port communicating with at least one of the inlet-side channels, wherein a first inlet-side channel extending inwardly from a first side of the inlet body is in communication with at least two other inlet-side channels extending inwardly from different sides of the inlet body than the first side of the inlet body;
an outlet-side microfluidic device comprising an outlet body having a plurality of outlet-side channels and a plurality of outlet-side ports, each outlet-side port communicating with at least one of the outlet-side channels, wherein a first outlet-side channel extending inwardly from a first side of the outlet body is in communication with at least two other outlet-side channels extending inwardly from different sides of the outlet body than the first side of the outlet body;
a column comprising a column inlet coupled to a first inlet-side port of the plurality of inlet-side ports, and a column outlet coupled to a first outlet-side port of the plurality of outlet-side ports; and
a flow controller (FC) comprising at least one FC input port for receiving a flow of a carrier gas, a first FC output port communicating with the at least one FC input port, and a second FC output port communicating with the at least one FC input port, wherein the first FC output port communicates with an additional inlet-side port of the plurality of inlet-side ports in communication with the column inlet of the column.

2. The GC unit of claim 1, wherein the second FC output port communicates with an additional outlet-side port of the plurality of outlet-side ports.

3. The GC unit of claim 2, wherein the first FC output port communicates with at least two of the inlet-side ports.

4. The GC unit of claim 2, wherein the second FC output port communicates with at least two of the outlet-side ports.

5. The GC unit of claim 2, wherein the FC comprises a forward pressure controller configured for controlling a flow of carrier gas to the second FC output port.

6. The GC unit of claim 2, wherein the FC input port comprises a first carrier gas line communicating with the first FC output port, a mass flow controller configured for controlling a first carrier gas flow from the FC input port to the first FC output port, a second carrier gas line communicating with the second FC output port, and a forward pressure controller configured for controlling a second carrier gas flow from the FC input port to the second FC output port.

7. The GC unit of claim 1, wherein the at least one FC input port comprises a first FC input port and a second FC input port, the at least one first FC input port communicates with the first FC-input port, the second FC input port communicates with the second FC output port, and the second FC output port is configured for venting gas from the GC unit.

8. The GC unit of claim 7, wherein the FC comprises a controller selected from the group consisting of: a mass flow controller configured for controlling a flow of carrier gas to the first FC output port; a back pressure controller configured for controlling a flow of gas from the second FC input port to the second FC output port; both of the foregoing.

9. A gas chromatographic (GC) device, comprising:
the GC unit of claim 1; and
a fluidic device selected from the group consisting of:
a sample introduction device communicating with at least one of the inlet-side ports;
an additional inlet-side microfluidic device communicating with at least one of the inlet-side ports;
a detector communicating with at least one of the outlet-side ports;
an additional outlet-side microfluidic device communicating with at least one of the outlet-side ports; and
two or more of the foregoing.

10. The GC unit of claim 1, wherein for each of the inlet-side microfluidic device and the outlet-side microfluidic device, the plurality of inlet-side or outlet-side ports comprises, in addition to the first inlet-side or outlet-side port, a second port, a third port, and a fourth port, and the plurality of channels comprises a first channel communicating with the first port, a second channel communicating with the second port, a third channel communicating with the third port, and a fourth channel communicating with the fourth port.

11. The GC unit of claim 10, wherein respective inside ends of the first channel, the second channel, the third channel, and the fourth channel, ending at interior positions inside the inlet block or the outlet block, are positioned such that the inside end of the second channel is between the inside end of the first channel and the inside end of the third channel, the inside end of the second channel is also between the inside end of the third channel and the inside end of the fourth channel, the inside end of the fourth channel is between the inside end of the first channel and the inside end of the second channel, and the inside end of the fourth channel is also between the inside end of the first channel and the inside end of the third channel.

12. The GC unit of claim 1, wherein at least one of the first FC output port and the second FC output port is reconfigurable to enable selection among a plurality of different flow paths through the first FC output port or the second FC output port.

13. The GC unit of claim 1, comprising a transfer line threadedly engaged with at least one microfluidic device of the inlet-side microfluidic device and the outlet-side microfluidic device.

* * * * *

UNITED STATES PATENT AND TRADEMARK OFFICE
CERTIFICATE OF CORRECTION

PATENT NO. : 9,921,191 B2
APPLICATION NO. : 14/721833
DATED : March 20, 2018
INVENTOR(S) : Xiao-Sheng Guan et al.

It is certified that error appears in the above-identified patent and that said Letters Patent is hereby corrected as shown below:

In the Specification

In Column 4, Line 30, delete "femtoliters" and insert -- femtolitres --, therefor.

In Column 14, Line 58, delete "that that" and insert -- that --, therefor.

In Column 19, Lines 5-6, delete "that that" and insert -- that --, therefor.

Signed and Sealed this
Twenty-second Day of May, 2018

Andrei Iancu
*Director of the United States Patent and Trademark Office*